(12) United States Patent
Hunter

(10) Patent No.: US 12,419,567 B2
(45) Date of Patent: Sep. 23, 2025

(54) DEVICES, SYSTEMS AND METHODS FOR USING AND MONITORING ORTHOPEDIC HARDWARE

(71) Applicant: CANARY MEDICAL SWITZERLAND AG, Baar (CH)

(72) Inventor: William L. Hunter, Vancouver (CA)

(73) Assignee: Canary Medical Switzerland AG, Baar (CH)

( * ) Notice: Subject to any disclaimer, the term of this patent is extended or adjusted under 35 U.S.C. 154(b) by 287 days.

(21) Appl. No.: 18/112,366

(22) Filed: Feb. 21, 2023

(65) Prior Publication Data

US 2023/0309906 A1     Oct. 5, 2023

Related U.S. Application Data

(63) Continuation of application No. 15/320,289, filed as application No. PCT/US2015/037827 on Jun. 25, 2015, now Pat. No. 11,596,347.

(Continued)

(51) Int. Cl.
| | |
|---|---|
| A61F 5/01 | (2006.01) |
| A61B 5/00 | (2006.01) |
| A61B 5/01 | (2006.01) |
| A61B 5/06 | (2006.01) |
| A61B 17/58 | (2006.01) |

(Continued)

(52) U.S. Cl.
CPC ............ *A61B 5/412* (2013.01); *A61B 5/0022* (2013.01); *A61B 5/01* (2013.01); *A61B 5/066* (2013.01); *A61B 5/067* (2013.01); *A61B 5/068* (2013.01); *A61B 5/4866* (2013.01); *A61B 5/6847* (2013.01); *A61B 17/58* (2013.01); *A61B 17/62* (2013.01); *A61B 17/68* (2013.01); *A61F 5/0102* (2013.01); *G16H 10/60* (2018.01); *G16H 15/00* (2018.01); *G16H 20/30* (2018.01); *G16H 40/40* (2018.01); *A61B 2017/00022* (2013.01)

(58) Field of Classification Search
CPC .. A61F 2/44; A61F 2/442; A61F 2/446; A61F 5/01; A61F 5/0102; G16H 15/00; G16H 40/40; G16H 20/30; G16H 10/60; A61B 5/00; A61B 5/41; A61B 5/412; A61B 17/58

See application file for complete search history.

(56) References Cited

U.S. PATENT DOCUMENTS

| | | |
|---|---|---|
| 4,161,782 A | 7/1979 | McCracken |
| 4,308,862 A | 1/1982 | Kalmar |

(Continued)

FOREIGN PATENT DOCUMENTS

| | | |
|---|---|---|
| CN | 1899222 A | 1/2007 |
| CN | 101257860 A | 9/2008 |

(Continued)

OTHER PUBLICATIONS

Ai-Fakih E., et al., "The Use of Fiber Bragg Grating Sensors in Biomechanics and Rehabilitation Applications: The State-of-the-Art and Ongoing Research Topics," Sensors, Sep. 25, 2012, vol. 12, No. 10, pp. 12890-12926.

(Continued)

*Primary Examiner* — Christopher J Beccia

(57) ABSTRACT

Orthopedic device or implants are provided, comprising an orthopedic device or implant and a sensor.

16 Claims, 16 Drawing Sheets

Related U.S. Application Data

(60) Provisional application No. 62/017,116, filed on Jun. 25, 2014.

(51) Int. Cl.

| | | |
|---|---|---|
| *A61B 17/62* | (2006.01) | |
| *A61B 17/68* | (2006.01) | |
| *G16H 10/60* | (2018.01) | |
| *G16H 15/00* | (2018.01) | |
| *G16H 20/30* | (2018.01) | |
| *G16H 40/40* | (2018.01) | |
| *A61B 17/00* | (2006.01) | |

(56) References Cited

U.S. PATENT DOCUMENTS

| | | |
|---|---|---|
| 4,411,266 A | 10/1983 | Cosman |
| 4,817,590 A | 4/1989 | Stancik, Jr. |
| 4,858,620 A | 8/1989 | Sugarman et al. |
| 4,862,878 A | 9/1989 | Davison et al. |
| 5,197,488 A | 3/1993 | Kovacevic |
| 5,413,604 A | 5/1995 | Hodge |
| 5,437,617 A | 8/1995 | Heinz et al. |
| 5,484,389 A | 1/1996 | Stark et al. |
| 5,593,409 A | 1/1997 | Michelson |
| 5,626,581 A | 5/1997 | Staehlin et al. |
| 5,672,954 A | 9/1997 | Watanabe |
| 5,733,292 A | 3/1998 | Gustilo et al. |
| 5,833,603 A | 11/1998 | Kovacs et al. |
| 5,906,643 A | 5/1999 | Walker |
| 6,019,794 A | 2/2000 | Walker |
| 6,053,882 A | 4/2000 | Johansen |
| 6,139,581 A | 10/2000 | Engh et al. |
| 6,245,109 B1 | 6/2001 | Mendes et al. |
| 6,358,202 B1 | 3/2002 | Arent |
| 6,447,448 B1 | 9/2002 | Ishikawa et al. |
| 6,565,573 B1 | 5/2003 | Ferrante et al. |
| 6,610,101 B2 | 8/2003 | Herr et al. |
| 6,706,071 B1 | 3/2004 | Wolter |
| 6,908,466 B1 | 6/2005 | Bonutti et al. |
| 7,009,511 B2 | 3/2006 | Mazar et al. |
| 7,044,951 B2 | 5/2006 | Medoff et al. |
| 7,097,662 B2 | 8/2006 | Evans, III et al. |
| 7,127,300 B2 | 10/2006 | Mazar et al. |
| 7,130,695 B2 | 10/2006 | Czygan et al. |
| 7,141,026 B2 | 11/2006 | Aminian et al. |
| 7,190,273 B2 | 3/2007 | Liao et al. |
| 7,333,013 B2 | 2/2008 | Berger |
| 7,383,071 B1 | 6/2008 | Russell et al. |
| 7,384,403 B2 | 6/2008 | Sherman |
| 7,450,332 B2 | 11/2008 | Pasolini et al. |
| 7,463,997 B2 | 12/2008 | Pasolini et al. |
| 7,491,188 B2 | 2/2009 | Holman et al. |
| 7,559,951 B2 | 7/2009 | DiSilvestro et al. |
| 7,686,808 B2 | 3/2010 | Orbay et al. |
| 7,789,897 B2 | 9/2010 | Sanders |
| 7,811,311 B2 | 10/2010 | Markworth et al. |
| 7,889,070 B2 | 2/2011 | Reeves et al. |
| 7,905,924 B2 | 3/2011 | White |
| 7,922,771 B2 | 4/2011 | Otto et al. |
| 7,924,267 B2 | 4/2011 | Sirtori |
| 8,029,566 B2 | 10/2011 | Lozier et al. |
| 8,048,134 B2 | 11/2011 | Partin |
| 8,075,627 B2 | 12/2011 | Caylor, III et al. |
| 8,080,064 B2 | 12/2011 | Dietz et al. |
| 8,083,741 B2 | 12/2011 | Morgan et al. |
| 8,109,890 B2 | 2/2012 | Kamiar et al. |
| 8,172,905 B2 | 5/2012 | Baynham et al. |
| 8,176,922 B2 | 5/2012 | Sherman et al. |
| 8,226,723 B2 | 7/2012 | Conti et al. |
| 8,244,368 B2 | 8/2012 | Sherman |
| 8,283,793 B2 | 10/2012 | Pless |
| 8,303,663 B2 | 11/2012 | Jimenez et al. |
| 8,311,632 B2 | 11/2012 | Pless et al. |
| 8,343,223 B2 | 1/2013 | Bucci |
| 8,361,121 B2 | 1/2013 | Barry |
| 8,361,131 B2 | 1/2013 | Chin et al. |
| 8,372,420 B2 | 2/2013 | Hunter et al. |
| 8,486,070 B2 | 7/2013 | Morgan et al. |
| 8,556,888 B2 | 10/2013 | Nields et al. |
| 8,562,671 B2 | 10/2013 | Neuenschwander |
| 8,634,808 B1 | 1/2014 | Zhong et al. |
| 8,634,928 B1 | 1/2014 | O'Driscoll et al. |
| 8,663,287 B2 | 3/2014 | Butler et al. |
| 8,668,742 B2 | 3/2014 | Caylor, III et al. |
| 8,721,643 B2 | 5/2014 | Morgan et al. |
| 8,728,160 B2 | 5/2014 | Globerman et al. |
| 8,876,739 B2 | 11/2014 | Salarian et al. |
| 8,996,892 B1 | 3/2015 | Chu et al. |
| 9,019,098 B2 | 4/2015 | Okano |
| 9,095,436 B2 | 8/2015 | Boyden et al. |
| 9,307,932 B2 | 4/2016 | Mariani et al. |
| 9,364,659 B1 | 6/2016 | Rao |
| 9,445,930 B2 | 9/2016 | Chen et al. |
| 9,456,915 B2 | 10/2016 | Chen et al. |
| 9,603,649 B2 | 3/2017 | Matyas et al. |
| 9,629,583 B2 | 4/2017 | Gradel et al. |
| 9,949,669 B2 | 4/2018 | DiSilvestro et al. |
| 10,070,973 B2 | 9/2018 | Sherman et al. |
| 10,219,699 B2 | 3/2019 | Wilder et al. |
| 10,285,637 B1 | 5/2019 | Hnat et al. |
| 10,499,855 B2 | 12/2019 | William |
| 10,582,891 B2 | 3/2020 | Wiedenhoefer et al. |
| 10,582,896 B2 | 3/2020 | Revie et al. |
| 10,898,106 B2 | 1/2021 | Bodewes et al. |
| 10,925,537 B2 | 2/2021 | Bailey et al. |
| 11,071,279 B2 | 7/2021 | Singh et al. |
| 11,191,479 B2 | 12/2021 | Bailey et al. |
| 11,684,260 B2 | 6/2023 | Wiedenhoefer et al. |
| 11,786,126 B2 | 10/2023 | Hunter et al. |
| 2001/0032059 A1 | 10/2001 | Kelly et al. |
| 2001/0050087 A1 | 12/2001 | Weissman et al. |
| 2002/0024450 A1 | 2/2002 | Townsend et al. |
| 2002/0026224 A1 | 2/2002 | Thompson et al. |
| 2002/0026226 A1 | 2/2002 | Ein |
| 2002/0049394 A1 | 4/2002 | Roy et al. |
| 2002/0107576 A1 | 8/2002 | Meyers et al. |
| 2002/0147416 A1 | 10/2002 | Zogbi et al. |
| 2002/0156529 A1 | 10/2002 | Li et al. |
| 2003/0069644 A1 | 4/2003 | Kovacevic et al. |
| 2003/0088385 A1 | 5/2003 | David |
| 2003/0196352 A1 | 10/2003 | Bledsoe et al. |
| 2003/0204267 A1 | 10/2003 | Hazebrouck et al. |
| 2004/0011137 A1 | 1/2004 | Hnat et al. |
| 2004/0019382 A1 | 1/2004 | Amirouche et al. |
| 2004/0019384 A1 | 1/2004 | Kirking et al. |
| 2004/0113790 A1 | 6/2004 | Hamel et al. |
| 2004/0204635 A1 | 10/2004 | Scharf et al. |
| 2004/0204766 A1 | 10/2004 | Siebel |
| 2004/0211580 A1 | 10/2004 | Wang et al. |
| 2004/0243148 A1 | 12/2004 | Wasielewski |
| 2004/0249464 A1 | 12/2004 | Bindseil et al. |
| 2004/0249471 A1 | 12/2004 | Bindseil et al. |
| 2005/0010299 A1 | 1/2005 | DiSilvestro |
| 2005/0010301 A1 | 1/2005 | DiSilvestro et al. |
| 2005/0012610 A1 | 1/2005 | Liao et al. |
| 2005/0021126 A1 | 1/2005 | Machan et al. |
| 2005/0065408 A1 | 3/2005 | Benderev |
| 2005/0149173 A1 | 7/2005 | Hunter et al. |
| 2005/0152945 A1 | 7/2005 | Hunter et al. |
| 2005/0165317 A1 | 7/2005 | Turner et al. |
| 2005/0187639 A1 | 8/2005 | Hunter et al. |
| 2005/0228410 A1 | 10/2005 | Berreklouw |
| 2005/0234555 A1 | 10/2005 | Sutton et al. |
| 2005/0242666 A1 | 11/2005 | Huscher et al. |
| 2005/0245992 A1 | 11/2005 | Persen et al. |
| 2005/0273170 A1 | 12/2005 | Navarro et al. |
| 2005/0288563 A1 | 12/2005 | Feliss et al. |
| 2006/0009856 A1 | 1/2006 | Sherman et al. |
| 2006/0024773 A1 | 2/2006 | Ohmiya et al. |
| 2006/0030771 A1 | 2/2006 | Levine et al. |
| 2006/0030945 A1 | 2/2006 | Wright |
| 2006/0036246 A1 | 2/2006 | Carl et al. |
| 2006/0047283 A1 | 3/2006 | Evans, III et al. |

(56) References Cited

U.S. PATENT DOCUMENTS

| | | |
|---|---|---|
| 2006/0052782 A1 | 3/2006 | Morgan et al. |
| 2006/0069403 A1 | 3/2006 | Shalon et al. |
| 2006/0079824 A1 | 4/2006 | Munch-Fals et al. |
| 2006/0079836 A1 | 4/2006 | Holman et al. |
| 2006/0100508 A1 | 5/2006 | Morrison |
| 2006/0111777 A1 | 5/2006 | Chen |
| 2006/0142670 A1 | 6/2006 | DiSilvestro et al. |
| 2006/0184067 A1 | 8/2006 | Clark et al. |
| 2006/0200121 A1 | 9/2006 | Mowery |
| 2006/0224088 A1 | 10/2006 | Roche |
| 2006/0229730 A1 | 10/2006 | Railey et al. |
| 2006/0247773 A1 | 11/2006 | Stamp |
| 2006/0271112 A1 | 11/2006 | Martinson et al. |
| 2006/0271199 A1 | 11/2006 | Johnson |
| 2006/0282168 A1 | 12/2006 | Sherman et al. |
| 2007/0004994 A1 | 1/2007 | Sherman |
| 2007/0005141 A1 | 1/2007 | Sherman |
| 2007/0049933 A1 | 3/2007 | Ahn et al. |
| 2007/0088442 A1 | 4/2007 | Cima et al. |
| 2007/0089518 A1 | 4/2007 | Ericson et al. |
| 2007/0100449 A1 | 5/2007 | O'Neil et al. |
| 2007/0118243 A1 | 5/2007 | Schroeder et al. |
| 2007/0179739 A1 | 8/2007 | Donofrio et al. |
| 2007/0233065 A1 | 10/2007 | Donofrio et al. |
| 2007/0233267 A1 | 10/2007 | Amirouche et al. |
| 2007/0234819 A1 | 10/2007 | Amirouche et al. |
| 2007/0238984 A1 | 10/2007 | Maschke et al. |
| 2007/0238992 A1 | 10/2007 | Donofrio et al. |
| 2007/0239282 A1 | 10/2007 | Caylor, III et al. |
| 2007/0265662 A1 | 11/2007 | Ufford |
| 2008/0027679 A1 | 1/2008 | Shklarski |
| 2008/0033527 A1 | 2/2008 | Nunez et al. |
| 2008/0065225 A1 | 3/2008 | Wasielewski et al. |
| 2008/0076972 A1 | 3/2008 | Dorogusker et al. |
| 2008/0088436 A1 | 4/2008 | Reeves et al. |
| 2008/0208516 A1 | 8/2008 | James |
| 2008/0214903 A1 | 9/2008 | Orbach |
| 2008/0215609 A1 | 9/2008 | Cleveland et al. |
| 2008/0300597 A1 | 12/2008 | Morgan et al. |
| 2008/0300659 A1 | 12/2008 | Matos |
| 2008/0306325 A1 | 12/2008 | Burnett et al. |
| 2008/0306407 A1 | 12/2008 | Taylor |
| 2008/0309481 A1 | 12/2008 | Tanaka et al. |
| 2009/0005708 A1 | 1/2009 | Johanson et al. |
| 2009/0005876 A1 | 1/2009 | Dietz et al. |
| 2009/0012372 A1 | 1/2009 | Burnett et al. |
| 2009/0048524 A1 | 2/2009 | Wildau et al. |
| 2009/0088756 A1 | 4/2009 | Anderson |
| 2009/0119222 A1 | 5/2009 | O'Neil et al. |
| 2009/0149964 A1 | 6/2009 | May et al. |
| 2009/0157146 A1 | 6/2009 | Linder et al. |
| 2009/0192533 A1 | 7/2009 | Dlugos, Jr. et al. |
| 2009/0198288 A1 | 8/2009 | Hoof et al. |
| 2009/0253587 A1 | 10/2009 | Fernandez |
| 2009/0254063 A1 | 10/2009 | Von Oepen et al. |
| 2009/0264894 A1 | 10/2009 | Wasielewski |
| 2009/0287255 A1 | 11/2009 | Erickson et al. |
| 2009/0299228 A1 | 12/2009 | Lozier et al. |
| 2009/0299327 A1 | 12/2009 | Tilson et al. |
| 2009/0299373 A1 | 12/2009 | Sisken |
| 2010/0014626 A1 | 1/2010 | Fennell et al. |
| 2010/0023108 A1 | 1/2010 | Toner et al. |
| 2010/0037731 A1 | 2/2010 | Li |
| 2010/0042121 A1 | 2/2010 | Schneider et al. |
| 2010/0100011 A1 | 4/2010 | Roche |
| 2010/0145337 A1 | 6/2010 | Janna et al. |
| 2010/0152621 A1 | 6/2010 | Janna et al. |
| 2010/0191100 A1 | 7/2010 | Anderson et al. |
| 2010/0204551 A1 | 8/2010 | Roche |
| 2010/0204802 A1 | 8/2010 | Wilson et al. |
| 2010/0262160 A1 | 10/2010 | Boyden et al. |
| 2010/0285082 A1 | 11/2010 | Fernandez |
| 2010/0287422 A1 | 11/2010 | Miyazaki |
| 2010/0312188 A1 | 12/2010 | Robertson et al. |
| 2010/0331663 A1 | 12/2010 | Stein |
| 2010/0331932 A1 | 12/2010 | Stevenson et al. |
| 2011/0004076 A1 | 1/2011 | Janna et al. |
| 2011/0004124 A1 | 1/2011 | Lessar et al. |
| 2011/0015693 A1 | 1/2011 | Williamson |
| 2011/0019595 A1 | 1/2011 | Magar et al. |
| 2011/0054272 A1 | 3/2011 | Derchak |
| 2011/0059234 A1 | 3/2011 | Byun et al. |
| 2011/0063094 A1 | 3/2011 | Meiertoberens et al. |
| 2011/0077736 A1 | 3/2011 | Rofougaran |
| 2011/0082393 A1 | 4/2011 | Bort |
| 2011/0087306 A1 | 4/2011 | Goossen |
| 2011/0092948 A1 | 4/2011 | Shachar et al. |
| 2011/0098576 A1 | 4/2011 | Hollstien |
| 2011/0158206 A1 | 6/2011 | Shrestha et al. |
| 2011/0196501 A1 | 8/2011 | Michelson |
| 2011/0213221 A1* | 9/2011 | Roche ............... A61B 5/4509 |
| | | 600/301 |
| 2011/0224564 A1 | 9/2011 | Moon et al. |
| 2011/0266265 A1* | 11/2011 | Lang ............... A61F 2/30756 |
| | | 219/121.72 |
| 2011/0288436 A1 | 11/2011 | Stone |
| 2011/0288805 A1 | 11/2011 | Dejnabadi et al. |
| 2011/0319755 A1 | 12/2011 | Stein et al. |
| 2012/0029316 A1 | 2/2012 | Raptis et al. |
| 2012/0123498 A1 | 5/2012 | Gross |
| 2012/0123716 A1 | 5/2012 | Clark |
| 2012/0130687 A1 | 5/2012 | Otto et al. |
| 2012/0191206 A1 | 7/2012 | Stein et al. |
| 2012/0216611 A1 | 8/2012 | Stein et al. |
| 2012/0220839 A1 | 8/2012 | Stein et al. |
| 2012/0226360 A1 | 9/2012 | Stein et al. |
| 2012/0226364 A1 | 9/2012 | Kampas et al. |
| 2012/0232662 A1 | 9/2012 | Jansen et al. |
| 2012/0283781 A1 | 11/2012 | Arnin |
| 2012/0313760 A1 | 12/2012 | Okano |
| 2012/0323333 A1 | 12/2012 | Metzger |
| 2013/0006367 A1 | 1/2013 | Bucci |
| 2013/0023795 A1 | 1/2013 | Stein et al. |
| 2013/0027186 A1 | 1/2013 | Cinbis et al. |
| 2013/0066426 A1 | 3/2013 | Martinson et al. |
| 2013/0079668 A1 | 3/2013 | Stein et al. |
| 2013/0079669 A1 | 3/2013 | Stein et al. |
| 2013/0079671 A1 | 3/2013 | Stein et al. |
| 2013/0079672 A1 | 3/2013 | Stein et al. |
| 2013/0079674 A1 | 3/2013 | Stein et al. |
| 2013/0079675 A1 | 3/2013 | Stein et al. |
| 2013/0079679 A1 | 3/2013 | Roche et al. |
| 2013/0079884 A1 | 3/2013 | Stein et al. |
| 2013/0109998 A1 | 5/2013 | Swoboda et al. |
| 2013/0110008 A1 | 5/2013 | Bourget et al. |
| 2013/0123684 A1 | 5/2013 | Giuffrida et al. |
| 2013/0144379 A1 | 6/2013 | Najafi et al. |
| 2013/0158669 A1 | 6/2013 | Sungarian et al. |
| 2013/0179110 A1 | 7/2013 | Lee |
| 2013/0197656 A1 | 8/2013 | Conrad |
| 2013/0215979 A1 | 8/2013 | Yakovlev et al. |
| 2013/0225949 A1 | 8/2013 | Roche |
| 2013/0231703 A1 | 9/2013 | Seme et al. |
| 2013/0252610 A1 | 9/2013 | Kim et al. |
| 2013/0270750 A1 | 10/2013 | Green |
| 2013/0317367 A1 | 11/2013 | Shuler |
| 2013/0329258 A1 | 12/2013 | Pettis et al. |
| 2013/0337256 A1 | 12/2013 | Farmer et al. |
| 2013/0338455 A1 | 12/2013 | Gradel et al. |
| 2013/0338770 A1 | 12/2013 | Boyden et al. |
| 2014/0009262 A1 | 1/2014 | Robertson et al. |
| 2014/0025338 A1 | 1/2014 | Blount et al. |
| 2014/0031063 A1 | 1/2014 | Park et al. |
| 2014/0034626 A1 | 2/2014 | Illston |
| 2014/0048970 A1 | 2/2014 | Batchelder et al. |
| 2014/0053956 A1 | 2/2014 | Etter et al. |
| 2014/0058289 A1 | 2/2014 | Panken et al. |
| 2014/0077421 A1 | 3/2014 | Minick |
| 2014/0085102 A1 | 3/2014 | McCormick |
| 2014/0135589 A1 | 5/2014 | Osorio |
| 2014/0135655 A1 | 5/2014 | Stein et al. |
| 2014/0180697 A1 | 6/2014 | Torok et al. |
| 2014/0256324 A1 | 9/2014 | Mohanty et al. |
| 2014/0257047 A1 | 9/2014 | Sillay et al. |

(56) References Cited

U.S. PATENT DOCUMENTS

| | | |
|---|---|---|
| 2014/0275849 A1 | 9/2014 | Acquista |
| 2014/0275861 A1 | 9/2014 | Kroh et al. |
| 2014/0288464 A1 | 9/2014 | Stein |
| 2014/0296663 A1 | 10/2014 | Boyden et al. |
| 2014/0303739 A1 | 10/2014 | Mentink et al. |
| 2014/0322935 A1 | 10/2014 | Filman et al. |
| 2014/0328253 A1 | 11/2014 | Lee et al. |
| 2014/0336764 A1 | 11/2014 | Masson et al. |
| 2014/0378872 A1 | 12/2014 | Hong et al. |
| 2014/0379090 A1 | 12/2014 | Diomidis et al. |
| 2015/0051455 A1 | 2/2015 | Wasielewski et al. |
| 2015/0057775 A1 | 2/2015 | Dong |
| 2015/0057967 A1 | 2/2015 | Albinali |
| 2015/0088253 A1 | 3/2015 | Doll et al. |
| 2015/0124675 A1 | 5/2015 | Farmer et al. |
| 2015/0202494 A1 | 7/2015 | Hollenbach et al. |
| 2015/0238304 A1 | 8/2015 | Lamraoui |
| 2015/0335290 A1 | 11/2015 | Hunter |
| 2016/0007909 A1 | 1/2016 | Singh et al. |
| 2016/0029952 A1 | 2/2016 | Hunter |
| 2016/0038087 A1 | 2/2016 | Hunter |
| 2016/0101281 A1 | 4/2016 | Chen |
| 2016/0128573 A1 | 5/2016 | Wilder et al. |
| 2016/0192878 A1 | 7/2016 | Hunter |
| 2016/0302721 A1 | 10/2016 | Wiedenhoefer et al. |
| 2016/0310066 A1 | 10/2016 | Wiedenhoefer et al. |
| 2016/0310077 A1 | 10/2016 | Hunter et al. |
| 2016/0338644 A1 | 11/2016 | Connor |
| 2016/0340177 A1 | 11/2016 | Takada |
| 2017/0035593 A1 | 2/2017 | Chen et al. |
| 2017/0042034 A1* | 2/2017 | MacCurdy .............. H05K 1/14 |
| 2017/0056722 A1 | 3/2017 | Singh et al. |
| 2017/0119472 A1 | 5/2017 | Herrmann et al. |
| 2017/0119566 A1 | 5/2017 | Chen et al. |
| 2017/0138986 A1 | 5/2017 | Kern |
| 2017/0156632 A1 | 6/2017 | Swiston et al. |
| 2017/0181825 A1 | 6/2017 | Hunter |
| 2017/0189553 A1 | 7/2017 | Hunter |
| 2017/0189752 A1 | 7/2017 | Mohrman et al. |
| 2017/0196478 A1 | 7/2017 | Hunter |
| 2017/0196499 A1 | 7/2017 | Hunter |
| 2017/0196508 A1 | 7/2017 | Hunter |
| 2017/0196509 A1 | 7/2017 | Hunter |
| 2017/0294949 A1 | 10/2017 | Zhang et al. |
| 2018/0028824 A1 | 2/2018 | Pivonka et al. |
| 2018/0125365 A1 | 5/2018 | Hunter et al. |
| 2018/0228428 A1 | 8/2018 | Anker et al. |
| 2018/0235546 A1 | 8/2018 | Hunter |
| 2019/0076273 A1 | 3/2019 | Goodchild et al. |
| 2019/0231555 A1 | 8/2019 | Neubardt |
| 2019/0247197 A1 | 8/2019 | Jagannathan et al. |
| 2020/0054215 A1 | 2/2020 | Roche |
| 2020/0155327 A1 | 5/2020 | Suh et al. |
| 2021/0077241 A1 | 3/2021 | Hunter |
| 2022/0387186 A1 | 12/2022 | Golemon, Jr. et al. |
| 2023/0285167 A1 | 9/2023 | Alva et al. |
| 2023/0301802 A1 | 9/2023 | Trousdale et al. |
| 2024/0156396 A1 | 5/2024 | Amiot et al. |

FOREIGN PATENT DOCUMENTS

| | | | |
|---|---|---|---|
| CN | 101495025 | A | 7/2009 |
| CN | 101536938 | A | 9/2009 |
| CN | 101773387 | A | 7/2010 |
| CN | 202036215 | U | 11/2011 |
| CN | 102740803 | A | 10/2012 |
| CN | 102885626 | A | 1/2013 |
| CN | 103313661 | A | 9/2013 |
| CN | 103458830 | A | 12/2013 |
| CN | 103735303 | A | 4/2014 |
| CN | 103957992 | A | 7/2014 |
| CN | 105283150 | A | 1/2016 |
| DE | 4322619 | C1 | 9/1994 |
| DE | 19924676 | A1 | 11/2000 |
| DE | 10342823 | A1 | 4/2005 |
| EP | 1147751 | A2 | 10/2001 |
| EP | 1382308 | A2 | 1/2004 |
| EP | 1382308 | A3 | 11/2005 |
| EP | 1803413 | A2 | 7/2007 |
| EP | 1803413 | A3 | 8/2008 |
| EP | 2018825 | A1 | 1/2009 |
| EP | 1814471 | B1 | 3/2010 |
| JP | 2005520630 | A | 7/2005 |
| JP | 2006055629 | A | 3/2006 |
| JP | 2007535372 | A | 12/2007 |
| JP | 2011514812 | A | 5/2011 |
| JP | 2022128381 | A | 9/2022 |
| KR | 20140133419 | A | 11/2014 |
| WO | 9733513 | A1 | 9/1997 |
| WO | 0149222 | A1 | 7/2001 |
| WO | 2004016204 | A1 | 2/2004 |
| WO | 2004091419 | A2 | 10/2004 |
| WO | 2005120203 | A2 | 12/2005 |
| WO | 2006105098 | A2 | 10/2006 |
| WO | 2006108065 | A2 | 10/2006 |
| WO | 2006113394 | A2 | 10/2006 |
| WO | 2008032316 | A2 | 3/2008 |
| WO | 2008035089 | A1 | 3/2008 |
| WO | 2008055229 | A2 | 5/2008 |
| WO | 2008103181 | A1 | 8/2008 |
| WO | 2008152549 | A2 | 12/2008 |
| WO | 2009083049 | A1 | 7/2009 |
| WO | 2009148847 | A2 | 12/2009 |
| WO | 2010040034 | A2 | 4/2010 |
| WO | 2011126706 | A2 | 10/2011 |
| WO | 2012061825 | A2 | 5/2012 |
| WO | 2012095784 | A1 | 7/2012 |
| WO | 2013022890 | A1 | 2/2013 |
| WO | 2013044160 | A2 | 3/2013 |
| WO | 2013096664 | A1 | 6/2013 |
| WO | 2013140147 | A1 | 9/2013 |
| WO | 2013152751 | A1 | 10/2013 |
| WO | 2013152805 | A1 | 10/2013 |
| WO | 2013155500 | A1 | 10/2013 |
| WO | 2013163585 | A1 | 10/2013 |
| WO | 2013179017 | A1 | 12/2013 |
| WO | 2014018100 | A1 | 1/2014 |
| WO | 2014020085 | A2 | 2/2014 |
| WO | 2014053956 | A1 | 4/2014 |
| WO | 2014071135 | A1 | 5/2014 |
| WO | 2014071968 | A1 | 5/2014 |
| WO | 2014074947 | A2 | 5/2014 |
| WO | 2014081594 | A1 | 5/2014 |
| WO | 2014083277 | A1 | 6/2014 |
| WO | 2014085170 | A1 | 6/2014 |
| WO | 2014100795 | A1 | 6/2014 |
| WO | 2014144070 | A1 | 9/2014 |
| WO | 2014144107 | A1 | 9/2014 |
| WO | 2014209916 | A1 | 12/2014 |
| WO | 2015021807 | A1 | 2/2015 |
| WO | 2015188867 | A1 | 12/2015 |
| WO | 2015200704 | A1 | 12/2015 |
| WO | 2015200707 | A1 | 12/2015 |
| WO | 2015200718 | A1 | 12/2015 |
| WO | 2015200720 | A2 | 12/2015 |
| WO | 2015200722 | A2 | 12/2015 |
| WO | 2015200723 | A1 | 12/2015 |
| WO | 2016065205 | A1 | 4/2016 |
| WO | 2016174612 | A1 | 11/2016 |
| WO | 2016180653 | A1 | 11/2016 |
| WO | 2016180654 | A1 | 11/2016 |
| WO | 2017165717 | A1 | 9/2017 |

OTHER PUBLICATIONS

Arami A., et al., "Accurate Measurement of Concurrent Flexion-Extension and Internal-External Rotations in Smart Knee Prostheses," IEEE Transactions on BioMedical Engineering, Sep. 2013, vol. 60, No. 9, pp. 2504-2510.

Arami A., et al., "Instrumented Prosthesis for Knee Implant Monitoring," IEEE International Conference on Automation Science and Engineering, Trieste, Italy, Aug. 24-27, 2011, pp. 828-835.

(56) References Cited

OTHER PUBLICATIONS

Bosch Press Release: "Bosch Sensortec Launches First IMU with Sub 1mA Current Consumption", Jun. 25, 2014, 3 Pages.
Bosch Sensortec: Bosch for BMI160 Small, Low—Power Inertial Measurement Unit, Jan. 15, 2015, 2 Pages.
Bosch Sensortec: "Data Sheet for BMI160 Small, Low Power Inertial Measurement Unit," Document Revision 0.8, Release Date Feb. 10, 2015, No. BST-BMI160-DS000-07, 110 Pages.
Chandrakasan A.P., et al., "Next Generation Micro-Power Systems," Symposium on VLSI Circuits Digest of Technical Papers, 2008, pp. 1-5, 04 pages.
Extended European Search Report for European Application No. 14817352.9, mailed Jun. 13, 2017, 15 Pages.
Extended European Search Report for European Application No. 15811139.3, mailed Aug. 9, 2018, 17 Pages.
Extended European Search Report for European Application No. 15811397.7, mailed Mar. 20, 2018, 13 Pages.
Extended European Search Report for European Application No. 15812631.8, mailed Nov. 12, 2018, 17 Pages.
Extended European Search Report for European Application No. 15842678.3, mailed Feb. 5, 2019, 13 Pages.
Extended European Search Report for European Application No. 17771204.9, mailed Feb. 28, 2020, 09 Pages.
Extended European Search Report for European Application No. 20171179.3, mailed Mar. 24, 2021, 18 Pages.
Forchelet D., et al., "Enclosed Electronic System for Force Measurements in Knee Implants," Sensors, Aug. 14, 2014, vol. 14, pp. 15009-15021.
Graichen F., et al., "Hip Endoprosthesis for in Vivo Measurement of Joint Force and Temperature," Journal of biomechanics, 1999, vol. 32, No. 10, pp. 1113-1117.
Heinlein B., et al., "Design, Calibration and Pre-clinical Testing of an Instrumented Tibial Tray," Journal of biomechanics, 2007, vol. 40, pp. S4-S10.
International Preliminary Report on Patentability for International Application No. PCT/US2015/037825, mailed Jan. 5, 2017, 08 Pages.
International Preliminary Report on Patentability for International Application No. PCT/US2015/037827, mailed Jan. 5, 2017, 09 Pages.
International Preliminary Report on Patentability for International Application No. PCT/US2015/050789, mailed Mar. 30, 2017, 07 Pages.
International Preliminary Report on Patentability for International Application No. PCT/US2017/023916, mailed Oct. 4, 2018, 20 Pages.
International Search Report and Written Opinion for International Application No. PCT/US2014/028381, mailed Jul. 7, 2014, 15 Pages.
International Search Report and Written Opinion for International Application No. PCT/US2014/043736, mailed Oct. 15, 2014, 15 Pages.
International Search Report and Written Opinion for International Application No. PCT/US2015/037825, mailed Dec. 8, 2015, 10 pages.
International Search Report and Written Opinion for International Application No. PCT/US2015/037827, mailed Dec. 8, 2015, 23 Pages.
International Search Report and Written Opinion for International Application No. PCT/US2015/050789, mailed Feb. 1, 2016, 10 Pages.
International Search Report and Written Opinion for International Application No. PCT/US2017/023916, mailed Aug. 2, 2017, 23 Pages.
Jacq C., et al., "Investigation of Polymer Thick-Film Piezoresistors for Medical Wrist Rehabilitation and Artificial Knee Load Sensors," Procedia Engineering, 2014, vol. 87, pp. 1194-1197.
Kroft S., "The Data Brokers: Selling your Personal Information," Extracted from Google on Sep. 4, 2014 is a script from "The Data Brokers" Aired on Mar. 9, 2014 on 60 Minutes CBS, pp. 1-8.
Loh N.C., et al., "Sub-10 cm3 Interferometric Accelerometer with Nano-g Resolution," Journal of Microelectromechanical Systems, vol. 11, No. 3, Jun. 2002, pp. 182-187.
Partial European Search Report for European Application No. 20171179.3, mailed Nov. 10, 2020, 16 Pages.
Partial Supplementary European Search Report for European Application No. 14762650.1, mailed Mar. 17, 2017, 08 Pages.
Partial Supplementary European Search Report for European Application No. 15811139.3, mailed Mar. 12, 2018, 16 Pages.
Partial Supplementary European Search Report for European Application No. 15842678.3, mailed Oct. 16, 2018, 15 Pages.
Polla D.L., et al., "Microdevices in Medicine," Annual Review Of Biomedical Engineering, 2000, vol. 02, pp. 551-576.
Ries M.D., "Endosteal Referencing in Revision Total Knee Arthroplasty," The Journal of Arthroplasty, 1998, vol. 13, No. 1, pp. 85-91.
Simoncini M., "Design And Integration Of An Instrumented Knee Prosthesis," Thesis No. 6379, 2014, Federal Polytechnic School of Lausanne, 162 Pages.
Singh U.K., et al., "Piezoelectric Power Scavenging of Mechanical Vibration Energy," Australian Mining Technology Conference, Oct. 2-4, 2007, pp. 111-118.
Xiang X., et al., "A Review of the Implantable Electronic Devices in Biology and Medicine," China Academic Journal Electronic Publishing House, vol. 32 (3), Mar. 3, 2004, pp. 462-467.
Yeh R., et al., "Single Mask, Large Force, and Large Displacement Electrostatic Linear Inchworm Motors," Journal of Microelectromechanical Systems, Aug. 4, 2002, vol. 11, No. 4, pp. 330-336, XP011064780.
Yiming L., et al., "Application of Wireless Sensor Networks in Healthcare," Chinese Journal of Medical Instrumentation, vol. 37 (5), Dec. 31, 2013, pp. 351-354 and Figure 1.
Yun K-S., et al., "A Surface-Tension Driven Micropump for Low-voltage and Low-Power Operations", Journal of Microelectromechanical Systems, Oct. 5, 2002, vol. 11, No. 5, pp. 454-461, DOI:10.1109/JMEMS.2002.803286, XP001192816.
European Search Report for European Application No. 23160709.4, mailed May 12, 2023, 8 Pages.
European Search Report for European Patent Application No. 24205658.8, dated Feb. 28, 2025, 9 Pages.

* cited by examiner

△ Accelerometer / Strain Gauge   ▥ Pressure Sensor
● Position Sensor / Location Marker   ★ Chemical sensor △ Accelerometer / Strain Gauge
● Position Sensor / Location Marker
▦ Pressure Sensor
✪ Chemical sensor △ Accelerometer / Strain Gauge
● Position Sensor / Location Marker
▦ Pressure Sensor
★ Chemical sensor

DEVICES, SYSTEMS AND METHODS FOR USING AND MONITORING ORTHOPEDIC HARDWARE

CROSS-REFERENCE TO RELATED APPLICATIONS

All applications for which a foreign or domestic priority claim is identified in the Application Data Sheet as filed with the present application are hereby incorporated by reference.

FIELD OF THE INVENTION

The present invention relates generally to orthopedic hardware, and more specifically, to devices and methods for monitoring the placement, efficacy, and performance of a wide variety of orthopedic hardware, including for example external hardware (e.g., casts, braces, tensors, slings and supports) and internal hardware [e.g., Kirschner-wires or "K-wires", pins, screws, plates, and intramedullary devices (e.g., rods and nails)].

BACKGROUND

The term "orthopaedics" was originally derived from the Greek word "orthos" (to correct or straighten), and "paidion" (meaning "child"). Hence, the field of orthopaedics (or orthopedics) was devoted to the treatment of children with deformities. Over time, the term became more widely associated with the treatment of diseases, disorders, and injuries associated with the musculoskeletal system (i.e., bones, muscles, cartilage, tendons, ligaments, joints, and other connective tissue that supports the body and allows motion). Common orthopedic conditions include musculoskeletal trauma (e.g., falls, motor vehicle accidents, etc.), sports injuries, degenerative diseases (such as various forms of arthritis), infections, tumors, and congenital disorders.

Orthopedic hardware has been developed to treat and/or assist in a wide variety of orthopedic procedures and surgeries; the term "hardware" being commonly used to describe implants used in the treatment of bone fractures and trauma to other musculoskeletal structures. Representative examples of orthopedic hardware include external hardware (e.g., casts, braces, tensors, external fixation devices, slings and supports), internal hardware (e.g., Kirschner-wires or "K-wires", pins, screws, plates, and intramedullary devices (e.g., rods and/or nails), devices utilized to deliver the hardware [e.g., tools and utensils (drills, chisels, mallets, tunneling catheters, etc.) used within the context of a surgical procedure] and/or devices and implants associated with (or used to affix) the hardware (e.g., bone cements, hemostats, sutures, adhesives and glues).

Unfortunately, when orthopedic surgery is performed, or when an orthopedic implant is applied or inserted, various complications may arise during the procedure (whether it is an open surgical procedure such as the placement of screws, plates or pins, or a minimally invasive procedure such as the percutaneous insertion of K wires or the application of external fixation). For example, during a fracture reduction procedure, the surgeon may wish to confirm correct anatomical alignment of the treated bones and/or detect any abnormal motion between the orthopedic implant and the surrounding bone tissue (or between the bone fragments themselves) so that corrective adjustments can be made during the procedure itself. In addition, to the extent the orthopedic device or implant is utilized in a surgical procedure, a physician may wish to confirm the correct placement of the device, and confirm the delivery of it to its final, desired anatomical location. Post-procedure, the patient may experience neurological symptoms, pain and ultimately non-union (the fractured bones do not heal back together) if there is abnormal movement between bone fragments (incomplete immobilization), migration of the device, bending or breakage of the device, or improper pressures and tensions present across the fracture plane.

In addition, long-term complications can develop after implantation of orthopedic hardware. For example, in the case of intramedullary rods (placed in the femur or tibia), 73.2% of all patients may have persistent or permanent knee pain, 27.3% may have atrophy of the calf muscle and/or quadriceps, and 35.4% may develop arthritis. In addition, deep vein thrombosis and pulmonary embolism can be common complications.

The present invention discloses novel orthopedic hardware which can overcome many of the difficulties and limitations found with previous orthopedic devices and implants, methods for constructing and monitoring these novel orthopedic devices and implants, and further provides other related advantages.

SUMMARY

Briefly stated, orthopedic devices and implants (also referred to as 'medical devices') are provided comprising an orthopedic device or implant along with one or more sensors to monitor the integrity and efficaciousness of the orthopedic device or implant. The sensors may be positioned on the inside of the orthopedic device or implant, within the body of the orthopedic device or implant, or on the outer surface (or surfaces) of the orthopedic device or implant, and/or between the orthopedic device or implant and any device that might be utilized to deliver the implant, as well as cements and glues that may also be utilized within a surgical procedure. Within certain embodiments, the sensors are of the type that are passive and thus do not require their own power supply.

According to various embodiments of the invention, the medical device comprises an orthopedic implant, along with one or more sensors. Examples of orthopedic devices and implants include external hardware (e.g., casts, braces, external fixation devices, tensors, slings and supports) and internal hardware [e.g., K-wires, pins, screws, plates, and intramedullary devices (e.g., rods and nails)]. In addition medical delivery devices for the placement of orthopedic devices and implants, along with one or more sensors, are also provided. Examples of medical delivery devices for orthopedic hardware include drills, drill guides, mallets, guidewires, catheters, bone tunneling catheters, microsurgical tools and general surgical tools. In addition, further components or compositions may be delivered along with the orthopedic implant and/or by the medical delivery device itself, and include fillers such as bone cement and polymers such as PMMA combined with one or more sensors. Within preferred embodiments of the above, the medical device, orthopedic implant, medical delivery device and filler are all provided in a sterile form (e.g., ETO sterilized), non-pyrogenic, suitable for use in humans and in a kit containing components suitable for a particular orthopedic surgery.

Representative examples of sensors suitable for use within the present invention include accelerometers (acceleration, tilt, vibration, shock and rotation sensors), pressure sensors, contact sensors, position sensors, chemical sensors, tissue metabolic sensors, mechanical stress sensors and temperature sensors. Within particularly preferred embodiments the sensor is a wireless sensor, or a sensor connected to a wireless microprocessor. Within further embodiments the orthopedic implant, implant, delivery device or surgical tool can have more than one type of the above-noted sensors.

According to various embodiments, sensors are placed at different locations in the orthopedic device or implant in order to monitor the operation, movement, medical imaging (both of the orthopedic device or implant and the surrounding tissues), function, physical integrity, wear, performance, potential side effects, medical status of the patient and the medical status of the orthopedic device or implant and its interface with the live tissue of the patient. Live, continuous, in situ, monitoring of patient activity, patient function, orthopedic device or implant activity, orthopedic device or implant function, orthopedic device or implant performance, orthopedic device or implant placement, orthopedic device or implant forces and mechanical stresses, orthopedic device or implant and surrounding tissue anatomy (imaging), mechanical and physical integrity of the orthopedic device or implant, and potential local and systemic side effects is provided. In addition, information is available on many aspects of the orthopedic device or implant and its interaction with the patient's own body tissues, including clinically important measurements not currently available through physical examination, medical imaging and diagnostic medical studies.

According to one embodiment, the sensors provide evaluation data of any motion or movement of the orthopedic device or implant. Motion sensors and accelerometers can be used to accurately determine the movement of the orthopedic implant and/or to determine if there is movement between bone (or tissue) fragments after surgical (or mechanical) reduction of a fracture during surgical placement, during medical and physical examination post-operatively, and during normal daily activities after the patient returns home.

According to another embodiment, contact sensors are provided between the orthopedic implant and the surrounding tissue and/or between articulated components of the device/implant itself. In other embodiments, vibration sensors are provided to detect the vibration between the orthopedic implant and the surrounding tissue and/or articulated components of the device/implant itself. In other embodiments, strain gauges are provided to detect the strain between the orthopedic implant and the surrounding tissue and/or between articulated components of the device/implant itself. Sudden increases in strain may indicate that too much stress is being placed on the orthopedic implant, which may increase damage to the body and/or breakage and damage to the device.

According to other embodiments, accelerometers are provided which detect vibration, shock, tilt and rotation of the device/implant and by extension the surrounding tissue itself. According to other embodiments, sensors for measuring surface wear, such as contact or pressure sensors, may be embedded at different depths within the orthopedic device or implant in order to monitor contact of the orthopedic device or implant with surrounding tissues, or degradation of the orthopedic device or implant over time (e.g., in the context of a biodegradable or bioerodible implants and devices). In other embodiments, position sensors, as well as other types of sensors, are provided which indicate potential problems such as movement, migration, pressure on surrounding anatomical structures, alignment, breakage, cracking and/or bending of the orthopedic device or implant in actual use over a period of time.

Within further embodiments, the orthopedic device or implant can contain sensors at specified densities in specific locations. For example, the orthopedic device or implant can have a density of sensors of greater than one, two, three, four, five, six, seven, eight, nine, or ten sensors [e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these] per square centimeter of the device/implant. Within other embodiments, the orthopedic device or implant can have a density of sensors of greater than one, two, three, four, five, six, seven, eight, nine, or ten sensors [e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these] per cubic centimeter of the device.

Within certain embodiments of the invention, the orthopedic device or implant is provided with a specific unique identifying number, and within further embodiments, each of the sensors on, in or around the orthopedic device or implant each have either a specific unique identification number, or a group identification number (e.g., an identification number that identifies the sensor as accelerometers (acceleration, tilt, vibration, shock and rotation sensors), pressure sensors, contact sensors, position sensors, chemical sensors, tissue metabolic sensors, mechanical stress sensors and temperature sensors). Within yet further embodiments, the specific unique identification number or group identification number is specifically associated with a position on, in or around the orthopedic device or implant.

Within other aspects of the invention methods are provided for monitoring an anatomically-implanted orthopedic device or implant comprising the steps of transmitting a wireless electrical signal from a location outside the body to a location inside the body; receiving the signal at a sensor positioned on, in or around an orthopedic device or implant located inside the body; powering the sensor using the received signal; sensing data at the sensor; and outputting the sensed data from the sensor to a receiving unit located outside of the body.

Within other aspects of the invention methods are provided for imaging an orthopedic device or implant as provided herein, comprising the steps of (a) detecting the location of one or more sensors in the orthopedic device or implant, any associated anatomical or radiological "landmarks", and/or associated medical delivery device or surgical tool; and (b) visually displaying the relative anatomical location of said one or more sensors, such that an image of the orthopedic implant is created. Within various embodiments, the step of detecting may be done over time, and the visual display may thus show positional movement over time. Within certain preferred embodiments the image which is displayed is a three-dimensional image.

The imaging techniques provided herein may be utilized for a wide variety of purposes. For example, within one aspect, the imaging techniques may be utilized during a surgical procedure in order to ensure proper anatomical placement and functioning of the orthopedic device or implant. Particularly in trauma surgery and fracture reduction, proper alignment and immobilization of the bone fragments is critical to obtaining a good outcome; therefore, allowing the surgeon to be able to see the implant's position in "real time" (particularly in procedures where direct vision is not possible) would be beneficial for achieving proper anatomical placement and immobilization. Within other embodiments, the imaging techniques may be utilized postoperatively in order to examine the orthopedic device or implant, and/or to compare operation, integrity, alignment and/or movement of the device/implant over time.

The integrity of the orthopedic device or implant can be wirelessly interrogated and the results reported on a regular basis. This permits the health and status of the patient to be checked on a regular basis or at any time as desired by the patient and/or physician. Furthermore, the orthopedic implant can be wirelessly interrogated when signaled by the patient to do so (via an external signaling/triggering device) as part of "event recording"—i.e. when the patient experiences a particular event (e.g. pain, injury, instability, etc.) she/he signals/triggers the device/implant to obtain a simultaneous reading in order to allow the comparison of subjective/symptomatic data to objective/sensor data. Matching event recording data with sensor data can be used as part of an effort to better understand the underlying cause or specific triggers of a patient's particular symptoms. Hence, within various embodiments of the invention, methods are provided for detecting and/or recording an event in a subject with one of the orthopedic device or implants provided herein, comprising the device/implant interrogation at a desired point in time. Within one aspect of the invention, methods are provided for detecting and/or recording an event in a subject with the orthopedic device or implant as provided herein, comprising the step of interrogating at a desired point in time the activity of one or more sensors within the orthopedic device or implant, and recording said activity. Within various embodiments, interrogation may be accomplished by the subject and/or by a health care professional. Within related embodiments, the step of recording may be performed with one or more wired devices, or, wireless devices that can be carried, or worn (e.g., a cellphone, watch or wristband, and/or glasses).

Within further embodiments, each of the sensors contains a signal-receiving circuit and a signal output circuit. The signal-receiving circuit receives an interrogation signal that includes both power and data collection request components. Using the power from the interrogation signal, the sensor powers up the parts of the circuitry needed to conduct the sensing, carries out the sensing, and then outputs the data to the interrogation module. The interrogation module acts under control of a control unit which contains the appropriate I/O circuitry, memory, a controller in the form of a microprocessor, and other circuitry in order to drive the interrogation module. Within yet other embodiments the sensors [e.g., accelerometers (acceleration, tilt, vibration, shock and rotation sensors), pressure sensors, contact sensors, position sensors, chemical sensors, tissue metabolic sensors, mechanical stress sensors and temperature sensors] are constructed such that they may readily be incorporated into, or otherwise mechanically attached to, the orthopedic device or implant (e.g., by way of a an opening or other appendage that provides permanent attachment of the sensor to the orthopedic device or implant) and/or readily incorporated into body of the orthopedic device or implant.

Within yet other aspects of the invention methods, devices are provided suitable for transmitting a wireless electrical signal from a location outside the body to a location inside the body; receiving the signal at one of the aforementioned sensors positioned on, in or around the orthopedic device or implant located inside the body; powering the sensor using the received signal; sensing data at the sensor; and outputting the sensed data from the sensor to a receiving unit located outside of the body. Within certain embodiments the receiving unit can provide an analysis of the signal provided by the sensor.

The data collected by the sensors can be stored in a memory located within the orthopedic device or implant, or on an associated device (e.g., an associated medical device, or an external device such as a cellphone, watch, wristband, and/or glasses). During a visit to the physician, the data can be downloaded via a wireless sensor, and the doctor is able to obtain data representative of real-time performance of the orthopedic implant, and any associated medical device.

The advantages obtained include more accurate monitoring of the orthopedic device or implant and permitting medical reporting of accurate, in situ, data that will contribute to the health of the patient. The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIG. 4A illustrates a knee brace; FIG. 4B a head and neck brace; FIG. 4C a neck brace; FIG. 4D a tensor bandage on the foot and ankle; FIG. 4E an arm sling; FIG. 4F a back brace.

FIG. 7A placement of cortical screws; FIG. 7B placement of cancellous screws; FIG. 7C placement of sensors on a full-threaded cortical screw; FIG. 7D placement of sensors on a full-threaded cancellous screw; and FIG. 7E, placement of sensors on a half-threaded cancellous screw.

FIG. 10B with contact or pressure sensors on the orthopedic hardware; and FIG. 10C with accelerometers on the orthopedic hardware.

DETAILED DESCRIPTION OF THE INVENTION

Figure 1A:
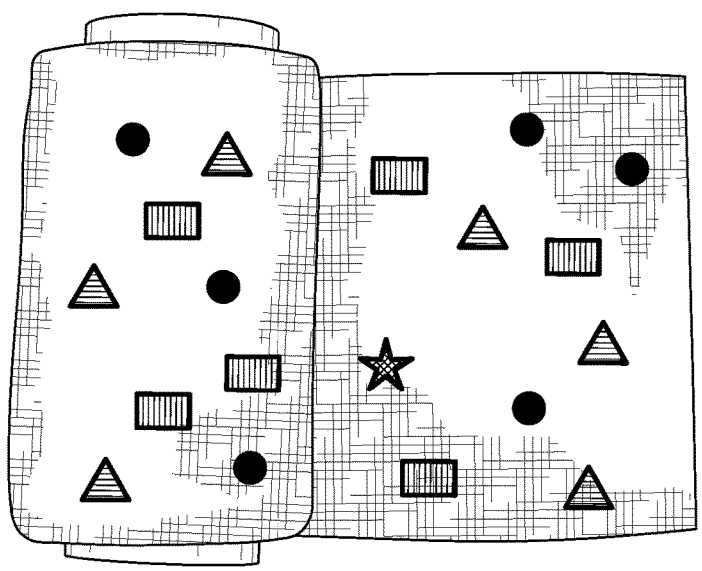
FIGS. 1A and 1B illustrate plaster and/or fiberglass casting material containing a variety of sensors, which can be wrapped to form a cast (FIG. 1B) to stabilize and immobilize a bone fracture.

Briefly stated the present invention provides a variety of orthopedic devices and implants that can be utilized to monitor the placement, location, anatomy, alignment, immobilization, performance, healing, integrity and/or efficaciousness of the orthopedic device or implant, and any associated medical devices and or device delivery instruments. Prior to setting forth the invention however, it may be helpful to an understanding thereof to first set forth definitions of certain terms that are used hereinafter.

"Orthopedic device and/or orthopedic implant" as those terms are utilized herein, refers to a wide variety of devices (typically hardware) and implants (typically biomaterials like bone cement, glues, adhesives, hemostats and bone grafts) that can be implanted into, around, or in place of part of a subject's musculoskeletal system (e.g., bone), in order to facilitate treatment of the disease, injury or disorder. Representative conditions that may be treated include musculoskeletal trauma (e.g., falls, trauma, motor vehicle accidents, projectile injuries), sports injuries, degenerative diseases (such as osteoarthritis and other forms of arthritis, osteoporosis), infections (osteomyelitis), tumors (primary and metastatic bone tumors), and congenital disorders (deformities, osteogenesis imperfect).

Orthopedic devices and implants can be utilized both externally and internally to correct musculoskeletal injuries and deformities. Representative examples of external orthopedic devices and implants include, for example: casts (e.g., made of plaster of paris, polyurenthane, fiberglass, or thermoplastics; see, e.g., U.S. Pat. Nos. 4,308,862, 4,817,590, 6,053,882), braces (see e.g., U.S. Pat. Nos. 4,862,878 and 5,437,617), tensor bandages (e.g., elastic bandages which are stretchable and can create localized pressure; e.g., Kendall Tensor Elastic Bandages), slings, supports and braces (e.g., ACE Adjusted Padded Sling, and Flexibrace®), (see generally "Orthopedic Taping, Wrapping, Bracing & Padding", Joel W. Beam, F.A. David Company, 2006).

Representative examples of internal hardware and implants include K-wires (Kirschner wires), pins (Steinmann pins), screws, plates, and intramedullary devices (e.g., rods and nails) and associated devices. Briefly, intramedullary rods or nails (including for example interlocking nails, Küntscher nails, Ender's nail, Grosse-Kempf (GK) nails, Gamma nails, and Rush nails) are long metal rods which are forced into the medullary cavity of a long bone (e.g., a femur, humerus, or tibia), thereby providing greater stability and support to the bone during healing. Kirschner wires (or "K-wires") are sharpened, smooth pins which are utilized to hold bone fragments together, or to serve as an anchor for skeletal traction. K-wires come in a variety of sizes and shapes, and within certain embodiments may be threaded. Orthopedic screws, pins and plates are utilized in a wide variety of orthopedic procedures to secure, stabilize, mend, fix, replace, or immobilize bone (or bone fragments). Representative orthopedic implants include Smith Peterson nails for fracture of the neck of the femur, McLaughin's plate (which along with Smith Peterson nails are used for intertrochanteric factures), Buttress plates for condylar fractures of the tibia, the Condylar blade plate for condylar fractures of the femur, Dynamic compression plates, Steinmann pin's for skeletal traction, Talwalkar nails for fractures of the radius and ulna, and Moore's pin for fractures of the head of the femur. Representative examples of the above devices, implants and devices are described in Oxford Textbook of Orthopedics and Trauma, Oxford University Press, 2002; (see also U.S. Pat. Nos. 6,565,573, 7,044,951, 7,686,808, 7,811,311, 7,905,924, 8,048,134, and 8,361,131) all of the above of which are incorporated by reference in their entirety.

Orthopedic devices or implants may be composed of a wide variety of materials (including for example metals such as titanium, titanium alloys, and/or stainless steel), although other materials can also be utilized, including polymers (e.g., polymethylmethacrylate or "PMMA", poly-ether-ether-ketone or "PEEK", and bone graft material that can be allographic, xenographic or synthetic); and non-polymeric materials such as silicon nitride.

Within certain embodiments of the invention, sensors can be placed into orthopedic devices which are traditionally made of metallic materials (e.g., plates) by a variety of different means. For example, within one embodiment small holes, cavities, or openings can be placed into a device (e.g., through use of a laser), and one or more sensor inserted into the opening. Within other embodiments, a surface of a metallic device can be coated with one or more polymers which contain or comprise one or more sensors.

"Orthopedic implant surgical device" or "orthopedic implant delivery device" refers to devices that can be utilized to introduce an orthopedic implant into a patient, and/or to surgical devices that can be utilized to operate on the bone. Representative examples include power drills, power screw devices, and power saw devices, mallets, hammers, and chisels all of which are composed of selected sterilizable components. Other examples include glue, hemostat, and bone cement injection devices.

The medical devices (e.g., orthopedic devices and implants, orthopedic delivery devices, etc.) and kits provided herein are preferably sterile, non-pyrogenic, and/or suitable for use and/or implantation into humans. However, within certain embodiments of the invention the medical devices and/or kits may be made in a non-sterilized environment (or even customized or "printed" for an individual subject), and sterilized at a later point in time.

"Sensor" refers to a device that can be utilized to measure one or more different aspects of a body tissue (anatomy, physiology, metabolism, and/or function) and/or one or more aspects of the orthopedic device or implant. Representative examples of sensors suitable for use within the present invention include, for example, fluid pressure sensors, fluid volume sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present invention. Representative patents and patent applications include U.S. Pat. Nos. 7,383,071, 7,450,332; 7,463,997, 7,924,267 and 8,634,928, and U.S. Publication Nos. 2010/0285082, and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," *J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 cm$^3$ Interferometric Accelerometer with Nano-g Resolution," *J. Microelectromechanical Sys.*, 11:3, June 2002, 182-187; all of the above of which are incorporated by reference in their entirety.

Within various embodiments of the invention the sensors described herein may be placed at a variety of locations and in a variety of configurations, on the inside of the orthopedic device or implant, within the body of the orthopedic device or implant, on the outer surface (or surfaces) of the orthopedic device or implant, between the orthopedic implant and any device an associated (or adjacent) orthopedic device or implant, and/or between the orthopedic implant and any device that might carry or deliver it (e.g., a delivery device, injection device, or surgical instrument). When the phrase "placed in the orthopedic implant" is utilized, it should be understood to refer to any of the above embodiments (or any combination thereof) unless the context of the usage implies otherwise.

The sensors may be placed in the orthopedic device or implant alone, or along with an associated medical device which might be utilized in a desired surgical procedure. For example, within certain embodiments, the orthopedic device or implant and/or orthopedic device or implant kit comprises sensors at a density of greater than 1, 2, 3, 4, 5, 6, 7, 8, 9, 10 or greater than 10 sensors per square centimeter. Within other aspects, the orthopedic device or implant and/or orthopedic device or implant kit comprises sensors at a density of greater than 1, 2, 3, 4, 5, 6, 7, 8, 9, 10 or greater than 10 sensors per cubic centimeter. Within either of these embodiments, there can be less than 50, 75, 100, or 100 sensors per square centimeter, or per cubic centimeter. Within various embodiments, at least one or more of the sensors may be placed randomly, or at one or more specific locations within the orthopedic device or implant, medical device, or kit as described herein.

In various embodiments, the sensors may be placed within specific locations and/or randomly throughout the orthopedic device or implant and/or associated devices. In addition, the sensors may be placed in specific patterns (e.g., they may be arranged in the pattern of an X, as oval or concentric rings around the orthopedic implant and/or associated devices).

Representative Embodiments of Orthopedic Device or Implants and Medical Uses of Sensor-Containing Orthopedic Device or Implants In order to further understand the various aspects of the invention provided herein, the following sections are provided below: A. Orthopedic device or implants and their Use; B. Use of Orthopedic device or implants to Deliver Therapeutic Agent(s); C. Methods for Monitoring Infection in Orthopedic device or implants; D. Further Uses of Sensor-containing Orthopedic device or implants in Healthcare; E. Generation of Power from Orthopedic device or implants; F. Medical Imaging and Self-Diagnosis of Assemblies Comprising Orthopedic device or implants, Predictive Analysis and Predictive Maintenance; G. Methods of Monitoring Assemblies Comprising Orthopedic device or implants; and H. Collection, Transmission, Analysis, and Distribution of Data from Assemblies Comprising Orthopedic device or implants.

A. Orthopedic Device or Implants and Their Use

A1. External Orthopedic Devices: Casts, Splints, Braces, Tensors, Slings and Supports As noted above, within various aspects of the invention, external orthopedic devices or implants and associated medical devices are provided for use in a wide variety of orthopedic procedures.

Figure 1B:
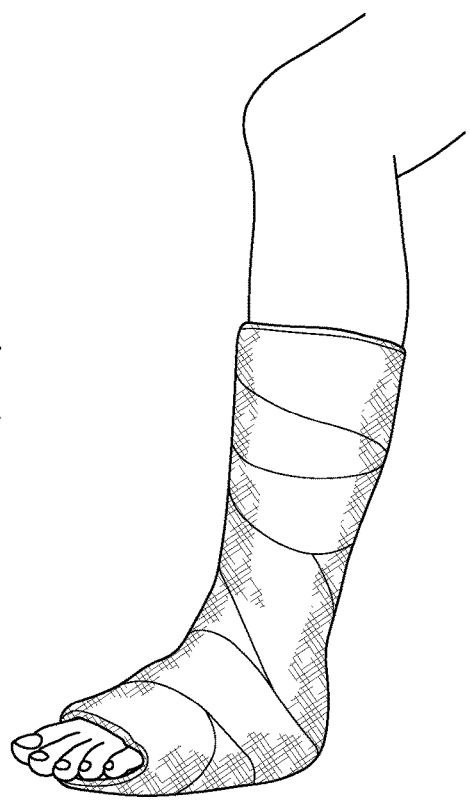
Figure 2:
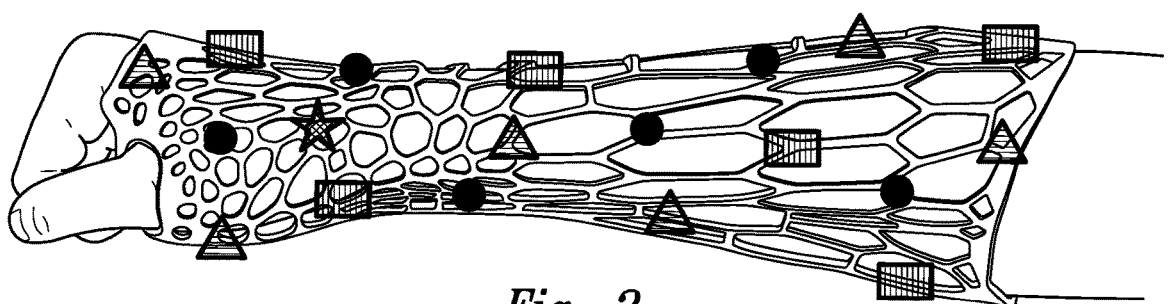
FIG. 2 illustrates representative sensors on a 3-D printed cast.

For example, as shown in FIG. 1A, a variety of sensors may be placed onto, within, and/or under casting material (e.g., typically plaster of paris on a mesh, fiberglass mesh, or a polymer-based composition such as polyurethane or a thermoplastic polymer), in order to form the cast shown in FIG. 1B. Similarly, as shown in FIG. 2, a wide variety of sensors may be placed on the surface of, within, and/or under the 3-D printed cast.

Such sensors can be utilized for a variety of purposes. For example, one of the complications associated with casts is the development of points of pressure between the cast and the skin, which can result in tissue sores, pain, and even tissue necrosis. Pressure sensors can be utilized to detect pressures during placement of the cast, as well as over the period that the cast is in place. The pressure sensors can be utilized to monitor inappropriate or dangerous increases in pressure (which can occur, for example, with inflammation occurring in the days following injury or after ambulation), and to serve as a basis to alert a patient, health care provider, or other entity or object as discussed in more detail below.

Accelerometers and/or position sensors can be utilized in casts in order to monitor joint movement and immobilization, and to ensure that too much stress is not placed on the casted body part. Proper fracture healing often requires not only immobilization of the bone fragments, but also the immobilization of the joints above and below the fracture. Accelerometers and/or position sensors can help to ensure that the underlying structure (e.g., bone) maintains proper alignment and that the related joints are adequately immobilized. In addition, the sensors can be utilized to monitor twisting, torque, flexion, extension and bending, all of which may lead to complications such as inadequate or improper healing.

Figure 3A:
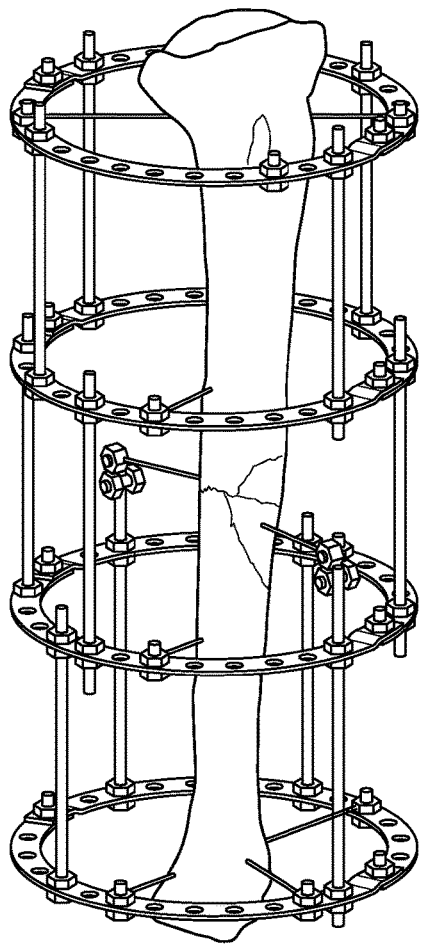
FIGS. 3A, 3B and 3C illustrate the use and placement of an external fixation device (including the use of screws, pins and clamps) on a bone (FIG. 3A), and an external fixation device containing a variety of sensors as placed on or into the radius (FIG. 3B) implanted on the arm (FIG. 3C).
Figure 3B:
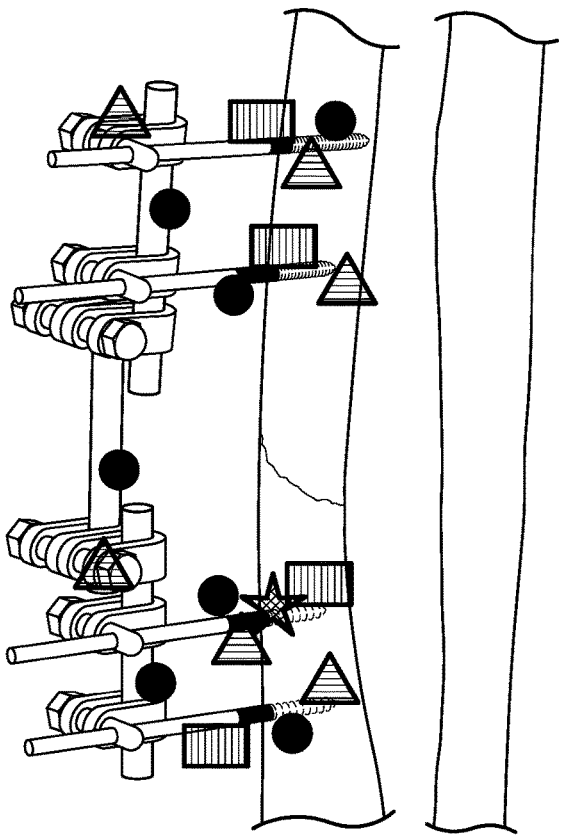
Figure 3C:
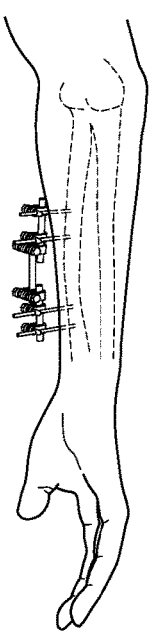

Within certain embodiments, external accelerometers and/or position sensors may be correlated with sensors which have been placed within the body (e.g., implanted by injection or surgically, or associated with an internal orthopedic implant as described in more detail below). For example, as shown in FIG. 3, external sensors (e.g. accelerometers, position sensors, pressure sensors) can be placed on an external support structure (e.g. see FIG. 3A). Sensors (e.g. accelerometers, position sensors, pressure sensors) can be placed on various aspects of the support structure (including for example on external screws, pins, clamps or other supporting structures), as well as on various aspects of the orthopedic devices or implants inserted on or into a bone (e.g., the radius as shown in FIG. 3B) implanted on the arm (FIG. 3C). Movement between the internal (implanted) sensors and external sensors can be utilized to assess whether anatomical segments have become misaligned, and whether such misalignment might need to be adjusted or corrected in a further procedure.

Within yet other embodiments chemical and temperature sensors can be utilized to monitor skin temperature, skin integrity, and/or the presence of an infection or a developing infection. Sensors positioned on casts and splints in contact with the skin are ideally located to serve this function.

Figure 4A:
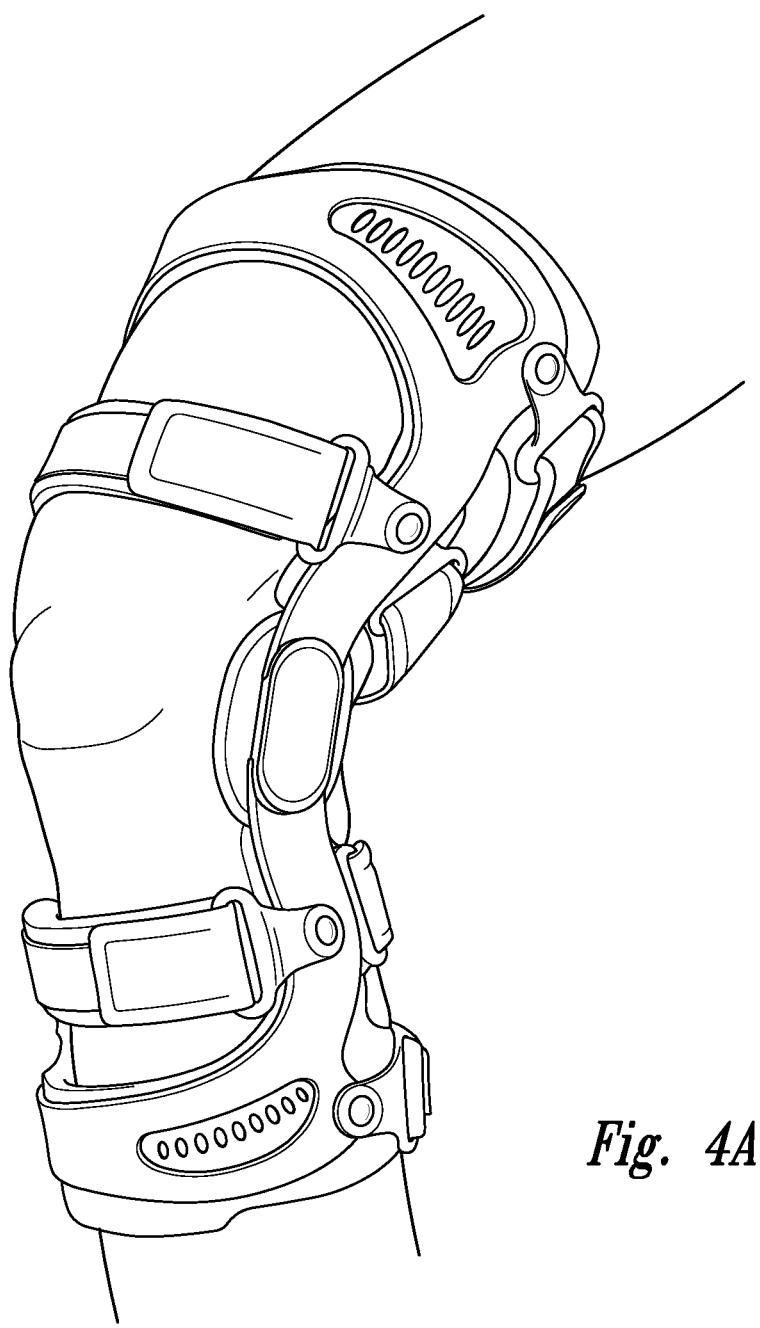
FIGS. 4A, 4B, 4C, 4D, 4E and 4F illustrate a variety of braces and slings.
Figure 4B:
Figure 4C:
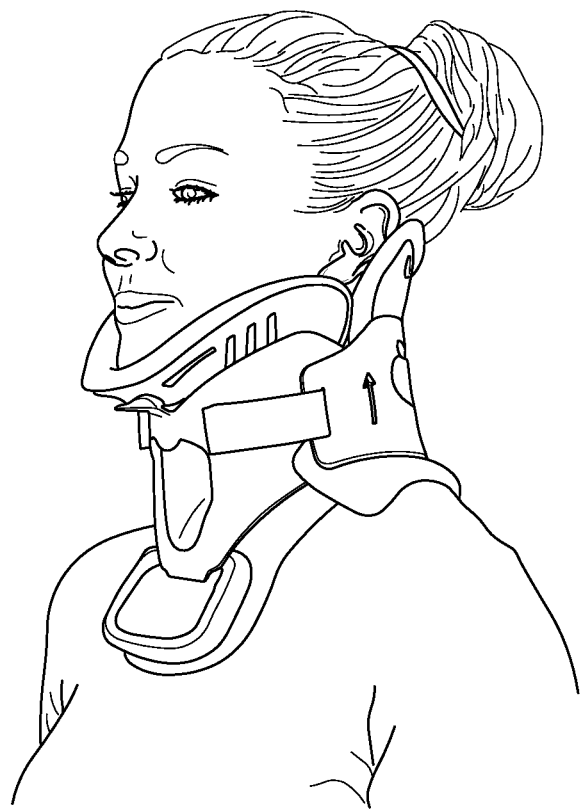
Figure 4D:
Figure 4E:
Figure 4F:
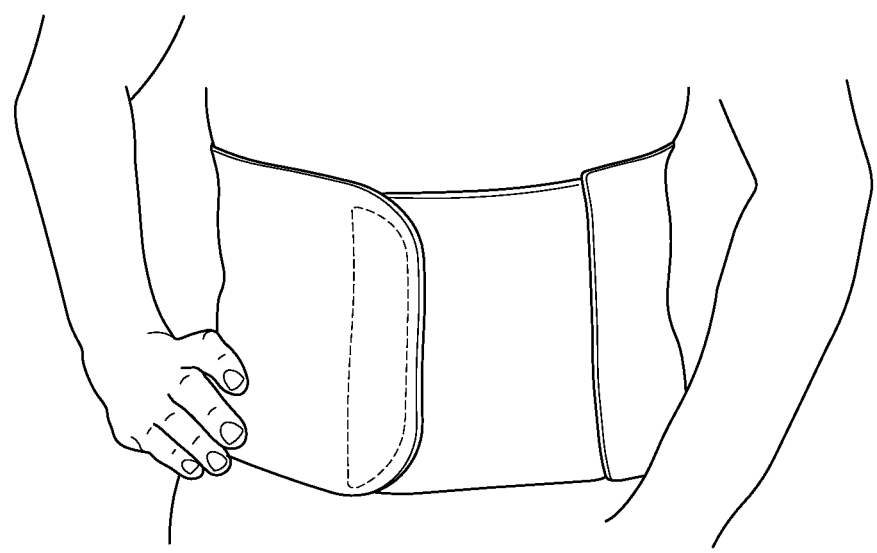

Within other embodiments of the invention, sensors can be placed on a variety of supports, braces, slings, splints and tensors. For example, as shown in FIG. 4, sensors can be placed on knee braces (FIG. 4A), head and neck braces (FIG. 4B), neck braces (FIG. 4C), tensor bandages (FIG. 4D), arm slings (FIG. 4E) and back braces (FIG. 4F).

Within various embodiments, pressure sensors can be placed in any of the braces, tensors, slings or supports provided herein. Pressure sensors can be placed within discrete locations, or located throughout the device. They can be utilized to measure compression, rotation and axial loading, and the amount of support. Detection of increased pressure can indicate the possibility of, or potential for, skin and or tissue damage. Detection of decreased pressure can indicate that the device might be ineffective and/or need reapplication or replacement. A rapid increase or decrease in pressure can indicate a traumatic event. For example, detection of a rapid increase in pressure could indicate swelling, inappropriate motion, and/or a risk of breakage or injury, or even the development of a compartment syndrome. A rapid decrease in pressure could indicate a total failure of the device.

Within other embodiments of the invention, accelerometers (and strain gauges) can be placed in any of the braces, tensors, slings, splints or supports provided herein. Accelerometers (and strain gauges) can be provided within discrete locations, or located throughout the device. Accelerometers can be utilized to monitor alignment, stability and healing. They can also be utilized to monitor and assess patient activity level (e.g., daily function, range of motion, physiotherapy, rehab and exercise), and to monitor for rotation, bending, breakage, movement and/or slippage of the device.

Within other embodiments of the invention, position sensors (and locations markers such as GPS) can be placed in any of the braces, tensors, slings, splints or supports provided herein. Position sensors (and location markers) can be provided within discrete locations, or located throughout the device. Such sensors can be utilized to monitor for example, any changes in anatomy, alignment, or mobility. In addition, through the use of location sensors, patient activity, compliance, mobility/immobility, the effect of rehab, and falls, breakage or emergencies can all be monitored.

Within yet other embodiments chemical and temperature sensors can be utilized to monitor skin temperature, skin integrity, and/or the presence of an infection or a developing infection.

In summary, a wide variety of sensors may be placed on and/or within the external orthopedic hardware described herein, in order to provide "real time" information and feedback to a health care provider (or a surgeon during a surgical procedure), to detect proper placement, anatomy, alignment, mobility/immobility (of injured tissues and related joints), forces exerted on surrounding tissues, and to detect the strain encountered in an surgical procedure. For example, the external orthopedic hardware provided herein (e.g., casts, splints, braces, tensors, slings and supports) can have one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide a 'real-world' activity (of affected limbs. joints etc.), fixation, mobility/immobility, healing, progressive rehabilitation and function and to collect and compare procedure performance data over time, to evaluate patient activity, and to better understand the conditions which implants are exposed to in the real world.

A2. Internal Orthopedic Hardware: K-wires, Pins, Screws, Plates, and Intramedullary Devices Within other aspects of the invention, sensors are provided in a wide variety of internal orthopedic devices. For example, Kirschner-wires or "K-wires", pins, screws, plates, and intramedullary devices (e.g., rods and nails) used to repair fractured, dislocated and injured musculoskeletal tissues.

A2.1 Pins

Figure 6:
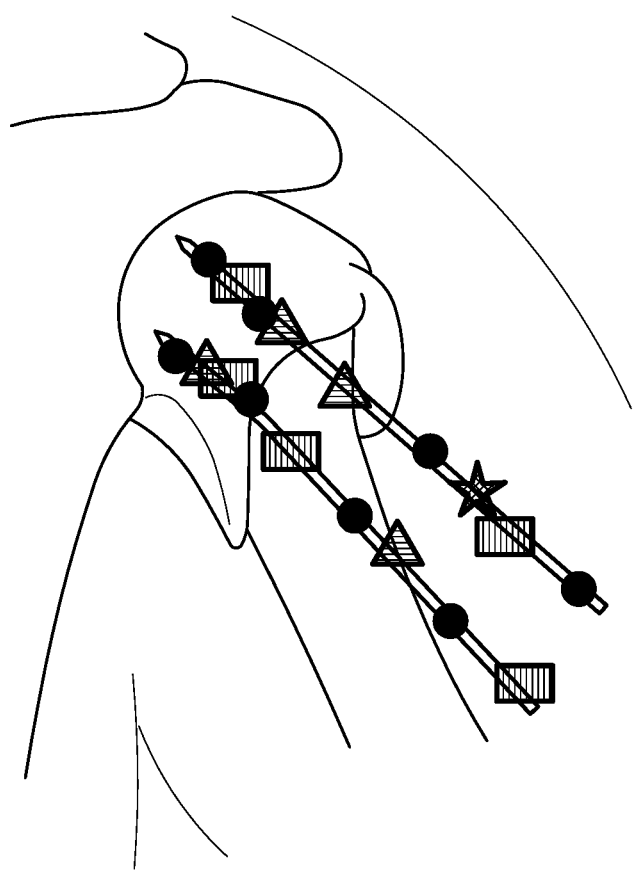
FIG. 6 illustrates one embodiment wherein a variety of sensors are placed on or within several pins (Steinmann pins) inserted to reduce a humeral fracture.

Pins are a common orthopedic device, and are commonly utilized as a way to stabilize bone fractures. One of the most common pins is the Steinmann Pin (also sometimes referred to as Intramedullary Pins or IM Pins), which is driven through the skin and into the bone in order to provide an anchor or support for the patient fracture. Most commonly, pins have either a two-sided (chisel) or a three-sided trocar tip (which is better suited to penetrating cortical bone). FIG. 6 illustrates one embodiment wherein a variety of sensors are placed on or within several pins.

Within one embodiment of the invention Pins are provided with one or more pressure sensors. The pressure sensors can be distributed on, or within the Pin at specific or randomized locations. Within certain embodiments they may be concentrated on the cutting end of the Pin. The pressure sensors can be useful during placement and removal (if necessary) of the Pin, during movement through different tissues [e.g., in order to determine soft tissue (low pressure), cortical bone (high pressure), cancellous bone (moderate pressure), marrow (low pressure), fracture planes (little to no pressure)—in order to assist in detection, placement and anatomical location].

Pressure sensors can also be useful after placement of a Pin. For example, detection of increased pressure on the Pin, or across the fracture plane, can indicate the potential for stress shielding (e.g., a reduction of bone density due to too much stress being borne by the implant and not enough being borne by the bone tissue) and/or increased potential for the Pin to bend, crack or break. Detection of increased pressure on the Pin in soft tissues can indicate the potential for the development of compartment syndrome. Detection of reduced pressure on the Pin, or across the fracture plane, can indicate the potential for non-union of the fracture (early in the healing process) or the successful completion of healing (later in the healing process when the bone has assumed normal support functions). Unequal and/or unbalanced pressures on the Pin, or across the fracture plane, can be a sign of poor alignment, shifting, and/or the application of torque on the healing bone. In all cases, identifying the presence of improper pressure forces across the fracture plane can allow for preemptive intervention to better stabilize the injury and prevent further damage to the bone.

Within other embodiments Pins are provided with accelerometers (and strain gauges). Similar to pressure sensors, accelerometers (and strain gauges) can be distributed on, or within the Pin at specific or randomized locations. However, within certain embodiments they may be concentrated on the cutting end of the Pin. The accelerometer sensors can be useful during placement and removal (if necessary) of the Pin by being able to detect movement through different tissues; they can also assist with achieving correct anatomical placement, alignment and imaging intraoperatively.

Accelerometers and strain gauges can also be useful after insertion of a Pin. For example, they can be utilized post-operatively to monitor alignment, stability, fragment mobility/immobility, healing, patient activities, stresses across the fracture, and related joint immobilization (or lack thereof).

Within another embodiment of the invention, Pins are provided with one or more position sensors/location marker sensors. The position sensors/location marker sensors can be distributed on, or within the Pin at specific or randomized locations. Within certain embodiments they may be concentrated on the cutting end of the Pin. The position sensors/location marker sensors can be useful during placement and removal (if necessary) of the Pin, during movement through different tissues (e.g., in order to determine soft tissue, cortical bone, cancellous bone, marrow, fracture planes—to assist in detection and determination of anatomical location, fracture anatomy, and correct post-surgical alignment), as well as in imaging and functional monitoring after placement.

Position sensors/location marker sensors can also be useful after placement of a Pin. For example, they can be utilized to monitor healing anatomy, and compare changes in location over time (e.g., post-surgery). They can also be utilized to monitor alignment, shifting and migration, to confirm joint immobilization, and to detect wire bending and/or breakage.

Within yet other embodiments of the invention, Pins are provided with temperature sensors and or chemical sensors. Briefly, temperature and/or chemical sensors can be utilized to monitor skin and tissue temperature, skin and tissue integrity, and/or the presence of an infection or a developing infection (e.g., bone infections (Osteomyelitis), and/or tissue necrosis).

As should be readily evident given the disclosure provided herein, the pins of the present invention can have one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide a 'real-world' alignment of the bone, to assist in detecting mobility/immobility of the fracture (and associated joints), to monitor healing and the development of complications, to collect and compare procedure performance data over time, to evaluate patient function, and to better understand the conditions which implants are exposed to in the real world.

A2.2 Kirschner Wires

Kirschner wires (or K-wires) are sharpened, sterilized steel wires that were originally developed by Martin Kirschner in 1909. K-wires came along after Steinmann Pins, when Dr. Kirschner recognized that larger pins caused more bone damage, as well as infection. Dr. Kirschner created his own device made of chrome piano wire to provide better tension when aligning fractured fragments of bone into place. Hence, the principle difference between wires and pins is one of size. Smaller diameters are referred to as wires and larger diameters are referred to as pins. Although there is no standardized definition of diameter cut off, typically pins are between 1.5 mm and 6.5 mm in diameter, wherein K-wires are 0.9 to 1.5 mm in diameter.

Figure 5:
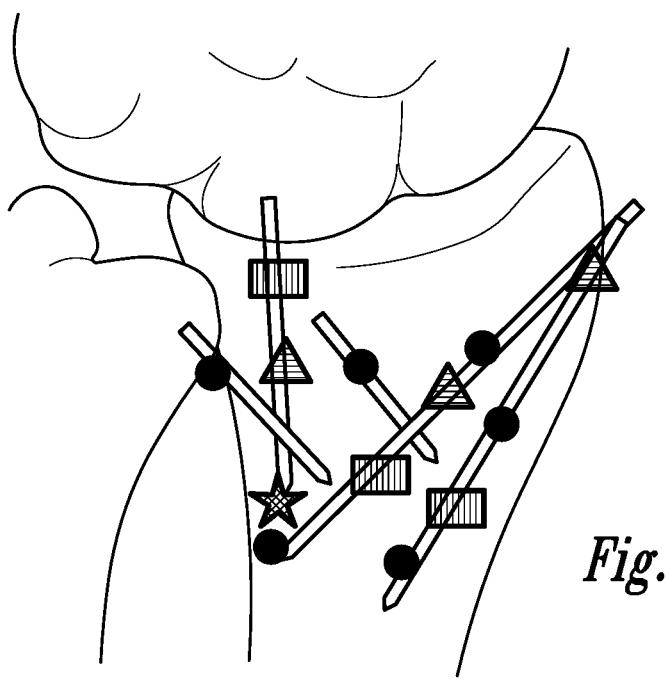
FIG. 5 illustrates one embodiment wherein a variety of sensors are placed on and/or within several K-wires (Kirschner wires) inserted to reduce a radial fracture.

K-wires are typically made of metal (e.g., stainless steel or nitinol), and come in a variety of sizes, diameters and lengths. They are commonly utilized to hold together bone fragments, to provide an anchor for skeletal fixation, or as a guide for screw placement, and are often driven into bone using a power or hand drill. FIG. 5 illustrates one embodiment wherein a variety of sensors are placed on and/or within several K-wires.

Within one embodiment of the invention K-wires are provided with one or more pressure sensors. The pressure sensors can be distributed on, or within the K-wire at specific or randomized locations. Within certain embodiments they may be concentrated on the cutting end of the K-wire. The pressure sensors can be useful during placement and removal (if necessary) of the K-wire, during movement through different tissues [e.g., in order to determine soft tissue (low pressure), cortical bone (high pressure), cancellous bone (moderate pressure), marrow (low pressure), fracture planes (little to no pressure)—in order to assist in detection, placement and anatomical location].

Pressure sensors can also be useful after placement of a K-wire. For example, detection of increased pressure on the K-wire, or across the fracture plane, can indicate the potential for stress shielding and/or increased potential for the Pin to bend, crack or break. Detection of increased pressure on the K-wire in soft tissues can indicate the potential for the development of compartment syndrome. Detection of reduced pressure on the K-wire, or across the fracture plane, can indicate the potential for non-union of the fracture (early in the healing process) or the successful completion of healing (later in the healing process when the bone has assumed normal support functions). Unequal and/or unbalanced pressures on the K-wire, or across the fracture plane, can be a sign of poor alignment, shifting, and/or the application of torque on the healing bone. In all cases, identifying the presence of improper pressure forces across the fracture plane can allow for preemptive intervention to better stabilize the injury and prevent further damage to the bone.

Within other embodiments K-wires are provided with accelerometers (and strain gauges). Similar to pressure sensors, accelerometers (and strain gauges) can be distributed on, or within the K-wire at specific or randomized locations. However, within certain embodiments they may be concentrated on the cutting end of the K-wire. The accelerometer sensors can be useful during placement and removal (if necessary) of the K-wire by being able to detect movement through different tissues; they can also assist with achieving correct anatomical placement, alignment and imaging intra-operatively.

Accelerometers and strain gauges can also be useful after insertion of a K-wire. For example, they can be utilized post-operatively to monitor alignment, stability, fragment mobility/immobility, healing, patient activities, stresses across the fracture, and related joint immobilization (or lack thereof).

Within another embodiment of the invention, K-wires are provided with one or more position sensors/location marker sensors. The position sensors/location marker sensors can be distributed on, or within the K-wire at specific or randomized locations. Within certain embodiments they may be concentrated on the cutting end of the K-wire. The position sensors/location marker sensors can be useful during placement and removal (if necessary) of the K-wire, during movement through different tissues (e.g., in order to determine soft tissue, cortical bone, cancellous bone, marrow, fracture planes—to assist in detection and determination of anatomical location, fracture anatomy, and correct post-surgical alignment), as well as in imaging and functional monitoring after placement.

Position sensors/location marker sensors can also be useful after placement of a K-wire. For example, they can be utilized to monitor healing anatomy, and compare changes in location over time (e.g., post-surgery). They can also be utilized to monitor alignment, shifting and migration, to confirm joint immobilization, and to detect wire bending and/or breakage.

Within yet other embodiments of the invention, K-wires are provided with temperature sensors and or chemical sensors. Briefly, temperature and/or chemical sensors can be utilized to monitor skin and tissue temperature, skin and tissue integrity, and/or the presence of an infection or a developing infection [e.g., bone infections (Osteomyelitis), and/or tissue necrosis].

As should be readily evident given the disclosure provided herein, the K-wires of the present invention can have one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide a 'real-world' alignment of the bone, to assist in detecting mobility/immobility of the fracture (and associated joints), to monitor healing and the development of complications, to collect and compare procedure performance data over time, to evaluate patient function, and to better understand the conditions which implants are exposed to in the real world.

A2.3 Screws

Bone screws are one of the most common devices used in orthopedic surgery. In 1850 two French surgeons (Cucel and Rigaud) are credited with performing the first internal fixation procedure with 2 transcutaneous screws fastened by string. Subsequently, in 1866 German surgeon Carl Hansmann performed an internal plate fixation using a removable steel plate and nickel-plated screws. It wasn't until the 1940s however that surgeons began to advocate for screws that were specifically designed for human bone. For example, Belgian surgeon Robert Danis proposed three key design features for bone screws: 1) a ratio of exterior diameter to core diameter of 3:2, not 4:3 as was typical to common metal screws; 2) a reduction of thread surface area to one-sixth that of metal screws (because bone is not as strong as metal); and 3) a buttress thread design to replace standard V-shaped threads, hence enhancing holding power.

Bone screws now come in a variety of sizes and shapes. They may be composed of a wide variety of polymers, metals and metal alloys, and a variety of shapes, configurations and sizes (e.g., polyaxial screws, monoaxial screws, locking screws, self-drilling screws, self-locking screws, self-tapping screws, cannulated screws, screws with a low-profile, hex heads, etc.).

Figure 7C:
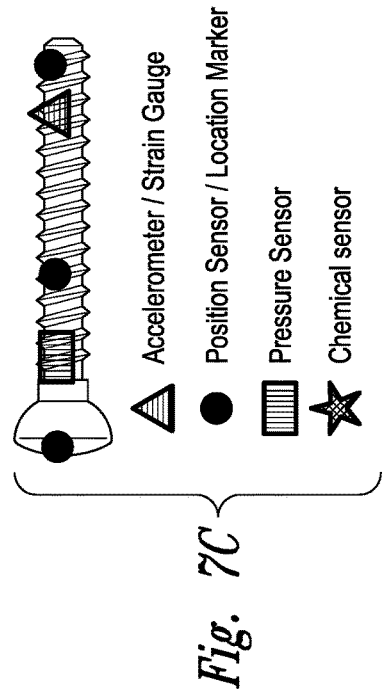
FIGS. 7A, 7B, 7C, 7D, and 7E illustrate a representative embodiment with respect to screws having sensors, including.
Figure 7D:
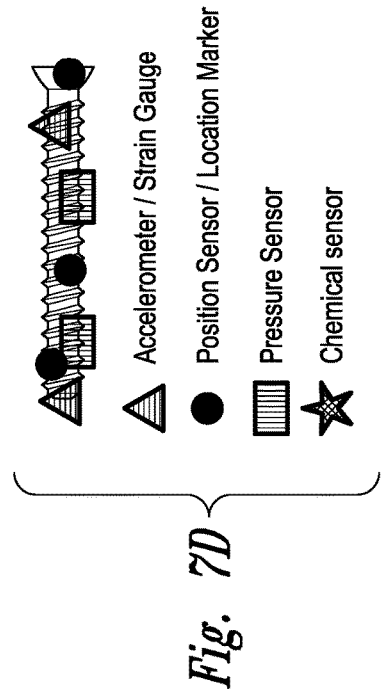
Figure 7E:
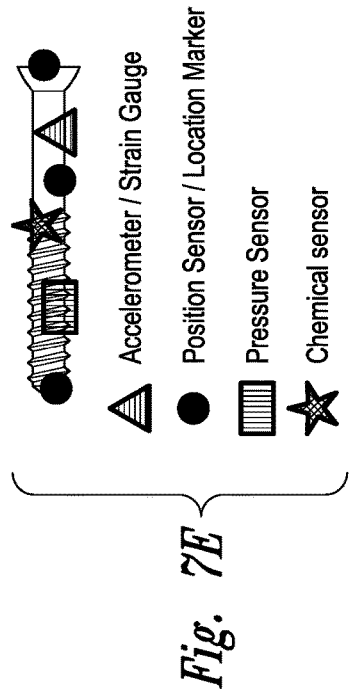
Figure 7B:
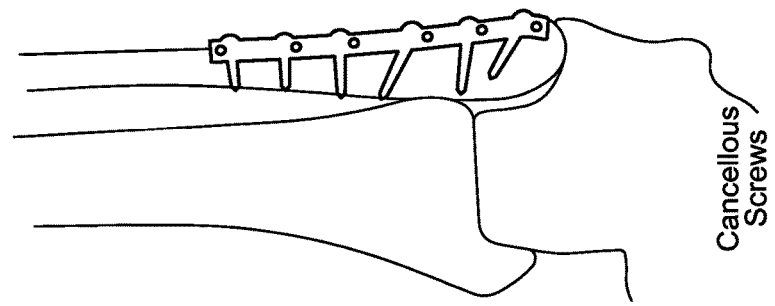
Figure 7A:
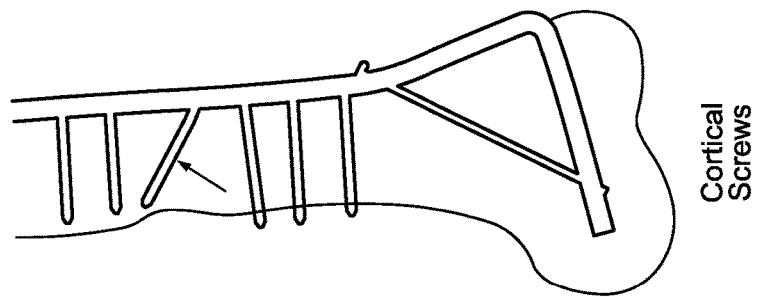

In addition, screws may be designed for a particular purpose. For example, cortical screws (for use in cortical bone) are typically fully threaded and require a tap to cut threads prior to insertion. FIG. 7C illustrates one embodiment wherein sensors are placed on or within a cortical screw. FIG. 7A illustrates the use of cortical screws in a subject.

Cancellous screws (which are designed for cancellous bone) are typically self-tapping screws with a relatively thin core and wide deep threads. They may be fully threaded (e.g., ideally for use in fastening devices such as plates into the metaphyseal or epiphyseal areas of bone), or partially threaded (they may be utilized for an area far from the cortex, but do not, however, have as much holding power). FIG. 7D illustrates the placement of sensors on a full-threaded cancellous screw, and FIG. 7E illustrates the placement of sensors on a half-threaded cancellous screw. FIG. 7B illustrates the placement of cancellous screws in a subject.

Figure 8A:
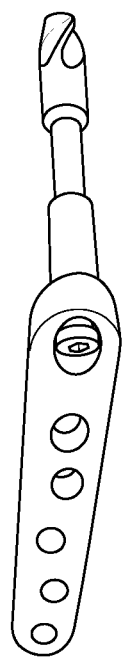
FIGS. 8A, 8B and 8C illustrate representative dynamic hip screws, including a sideplate with a reamer inserted to prepare a hole (FIG. 8A), cortical screws inserted into the sideplate (FIG. 8B), and an illustration of the device inserted into a subject (FIG. 8C).
Figure 8B:
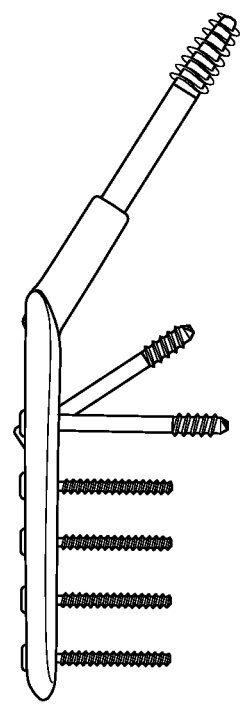
Figure 8C:
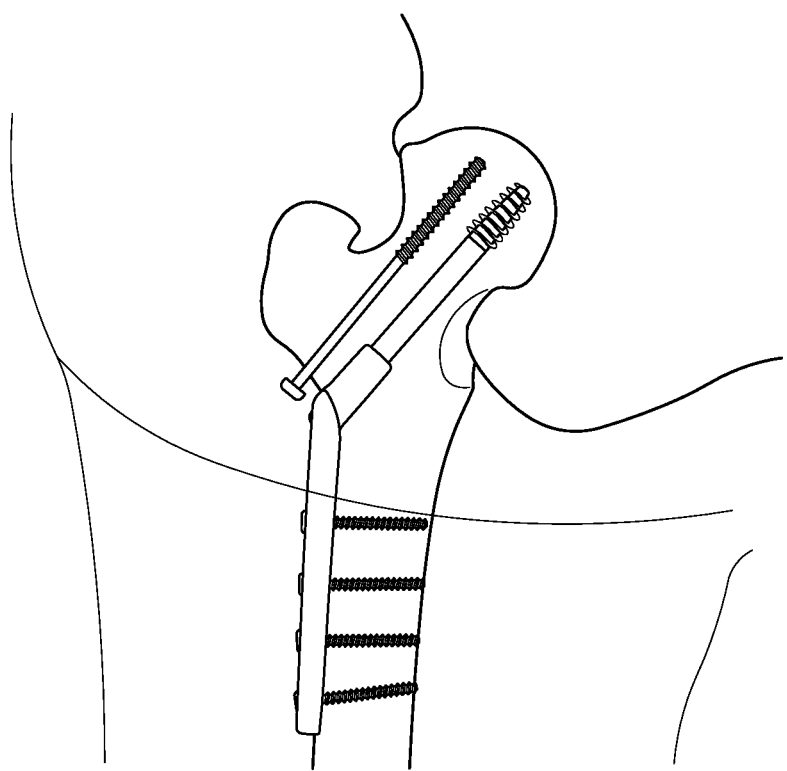

In addition to more common screw types (such as the cancellous and cortical screws), there are a large number of specialty bone screws. For example, dynamic hip screws ("DHS") are a type of orthopedic implant composed of a plate, along with different types of bone screws that are specifically designed for certain types of hip fractures (typically intertrochanteric fractures). More specifically, as shown in FIG. 8A, a DHS side plate is aligned to a joint (e.g., a broken femoral head), and a hole is prepared utilizing a reamer. A sideplate, lag screw and cortical screws (FIG. 8B) are attached to the bone as shown in FIG. 8C. The idea of this implant is to cause dynamic compression of the femur and the femoral head, causing them to move along one plane (thereby hopefully allowing the native femur to undergo remodeling and proper fracture healing).

Other specialty bone screws include the Herbert screws and Acutrak screws which are cannulated and threaded at both ends, and typically utilized in fractures of small articular bones (e.g., carpal and scaphoid fractures). Interference screws can be specifically designed for certain procedures (e.g., soft tissue and bone-tendon-bone grafts), and are commonly comprised of polymers (e.g., PLDLA) and other components (e.g., Tri-Calcium Phosphate), (see, e.g., U.S. Patent Pub. No. 2009/0198288).

Within one embodiment of the invention pressure sensors are provided on or within a bone screw (e.g., cancellous or cortical screw, interference screw, or dynamic hip screw). The pressure sensors can be positioned within specific locations (e.g., at the point and/or head), or distributed throughout the screw. They can be utilized to assist in implanting the screw by detecting various tissue types (e.g., cancellous/cortical bone and bone marrow), detecting fracture planes, and assisting in the determination of anatomy and location. They can also be utilized to prevent accidental placement (e.g., into the articular cartilage; i.e. the pressure would drop from higher to lower when the screw moved from cortical bone into the articular cartilage). For example, detection of increased pressure on the screw, or across the fracture plane, can indicate the potential for stress shielding and/or increased potential for the screw to bend, crack or break. Detection of two much pressure on a DHS can be an indicator of impaction (with the risk of bone shortening). Detection of reduced pressure on the screw, or across the fracture plane, can indicate the potential for non-union of the fracture (early in the healing process) or the successful completion of healing (later in the healing process when the bone has assumed normal support functions; monitoring this can be helpful in determining the timing of ambulation). Unequal and/or unbalanced pressures on the K-wire, or across the fracture plane, can be a sign of poor alignment, shifting, and/or the application of torque on the healing bone. In all cases, identifying the presence of improper pressure forces across the fracture plane can allow for preemptive intervention to better stabilize the injury and prevent further damage to the bone.

Within another embodiment bone screws are provided with accelerometers (and strain gauges). Similar to pressure sensors, accelerometers (and strain gauges) can be distributed on, or within the bone screw at specific or randomized locations. However, within certain embodiments they may be concentrated on specific locations (e.g., the point or head of the screw). The accelerometer sensors can be useful during placement and removal (if necessary) of the screw by being able to detect movement through different tissues; they can also assist with achieving correct anatomical placement, alignment and imaging intraoperatively.

Accelerometers and strain gauges can also be useful after insertion of a screw. For example, they can be utilized post-operatively to monitor alignment, stability, fragment mobility/immobility, healing, patient activities, stresses across the fracture, and related joint immobilization (or lack thereof).

Within another embodiment of the invention, screws are provided with one or more position sensors/location marker sensors. The position sensors/location marker sensors can be distributed on, or within the screw at specific or randomized locations. Within certain embodiments they may be concentrated on the cutting end of the screw. The position sensors/location marker sensors can be useful during placement and removal (if necessary) of the screw, during movement through different tissues (e.g., in order to determine soft tissue, cortical bone, cancellous bone, marrow, fracture planes—to assist in detection and determination of anatomical location, fracture anatomy, and correct post-surgical alignment), as well as in imaging and functional monitoring after placement.

Position sensors/location marker sensors can also be useful after placement of a bone screw. For example, they can be utilized to monitor healing anatomy, and compare changes in location over time (e.g., post-surgery). They can also be utilized to monitor alignment, shifting and migration, to confirm joint immobilization, and to detect screw bending and/or breakage. Importantly, bone screws with position sensors/location markers can be utilized to detect movement (e.g., 'backing out') of the screw before serious complications arise. In DHS, lack of movement of the screw in the tunnel is a sign of non-union or of advancement of the screw into the articular cartilage, while excessive movement of the screw in the tunnel is inactive of shortening (and impaction). Similarly, for screws that are utilized with plates, a bone screw with sensors can be utilized to detect plate movement, and allow intervention prior to serious complications.

Within yet other embodiments of the invention bone screws are provided with temperature sensors and or chemical sensors. Briefly, temperature and/or chemical sensors can be utilized to monitor mineralization, tissue health, bleeding, tissue temperature, tissue health (such as avascular necrosis of the hip), and/or the presence of an infection or a developing infection [e.g., bone infections (Osteomyelitis), and/or tissue necrosis].

As should be readily evident given the disclosure provided herein, the bone screws of the present invention can have one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide a 'real-world' alignment of the bone, to assist in detecting mobility/immobility of the fracture (and associated joints), to monitor healing and the development of complications, to collect and compare procedure performance data over time, to evaluate patient function, and to better understand the conditions which implants are exposed to in the real world.

A2.4 Plates

Figure 9:
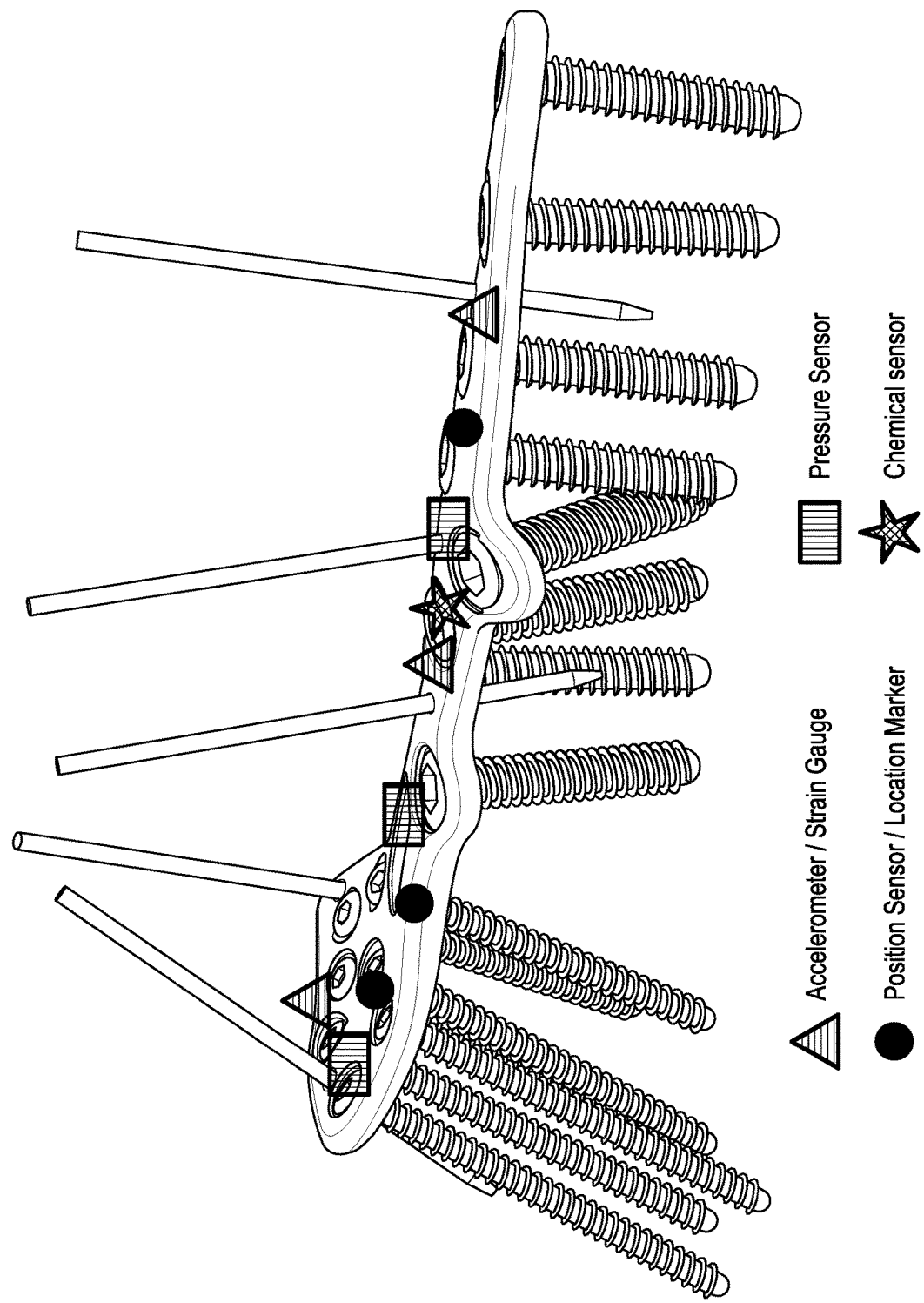
FIG. 9 illustrates an embodiment wherein sensors are placed on a representative fixation plate.

Orthopedic plates (also referred to as 'fixation plates' and 'trauma plates') have been utilized to fix fractures for over a hundred years. The first metal plate was introduced by Dr. Lane in 1895 for the internal fixation of fractures. FIG. 9 illustrates an embodiment wherein sensors are placed on a representative fixation plate.

Fixation plates now come in a wide variety of shapes and sizes, for a variety of specific indications. Representative examples include: 1) the DHS sideplate shown in FIG. 8 for the fixation of fractures at or near the femoral head; 2) DC plates (typically used for the ulna and radius repairs); 3) Buttress plates (e.g., for the repair of comminuted tibial fractures); L-Buttress plates (for complicated surgeries); 4) Clavicle Hook plates; 5) Clover Leaf plates; 6) Condylus Humerus Bone plates; and 7) Humerus and Tibial Compression plates (too name a few). Typically plates are comprised of metals such as stainless steel or titanium. One representative plate with a variety of sensors is depicted in FIG. 9.

Figure 10A:
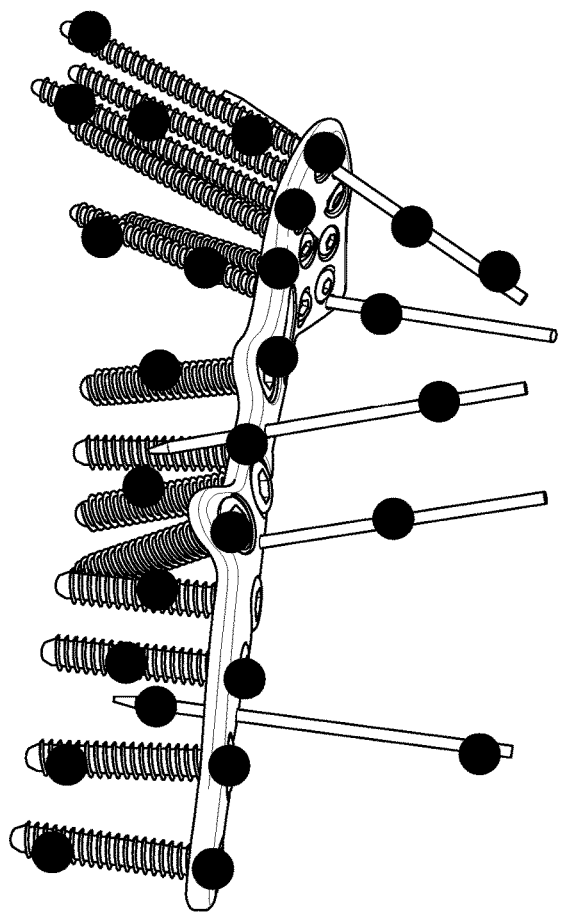
FIGS. 10A, 10B and 10C illustrate the placement of sensors in orthopedic hardware plates that can be utilized together with other orthopedic hardware (e.g., screws, wires, pins, rods and plates): including FIG. 10A with position sensors on the orthopedic hardware.
Figure 10B:
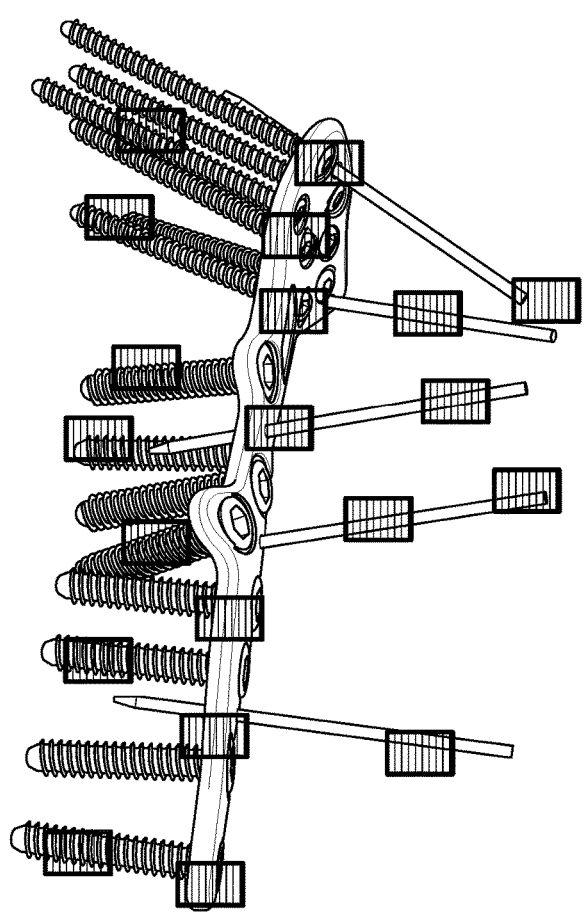

Within one embodiment of the invention pressure sensors are provided on or within a plate. As shown in FIG. 10B, pressure sensors can be positioned within specific locations (e.g., on the bone or tissue surface, around screw holes), or distributed throughout the plate. They can be utilized to assist in implanting the plate by detecting adherence to or contact with bone (e.g., for malleable plates like reconstruction plates), and or movement through tissue or bone during placement (e.g. on the chisel of blade plates). They can also be useful after placement. For example, detection of increased pressure can indicate the potential for stress shielding or the potential for bending cracking or fracture of the plate. Detection of increased pressure on the tissue surface could be an indicator of compartment syndrome. Detection of a rapid change in pressure can indicate plate breakage. Detecting a slow decrease in pressure can indicate that healing is occurring and can assist in decisions on weight bearing and rehabilitation. Monitoring the pressure around the screw holes can assist with appropriate tightening during placement; later it can be used to detect "backing out" of the screws or other complications such as breakage.

Figure 10C:
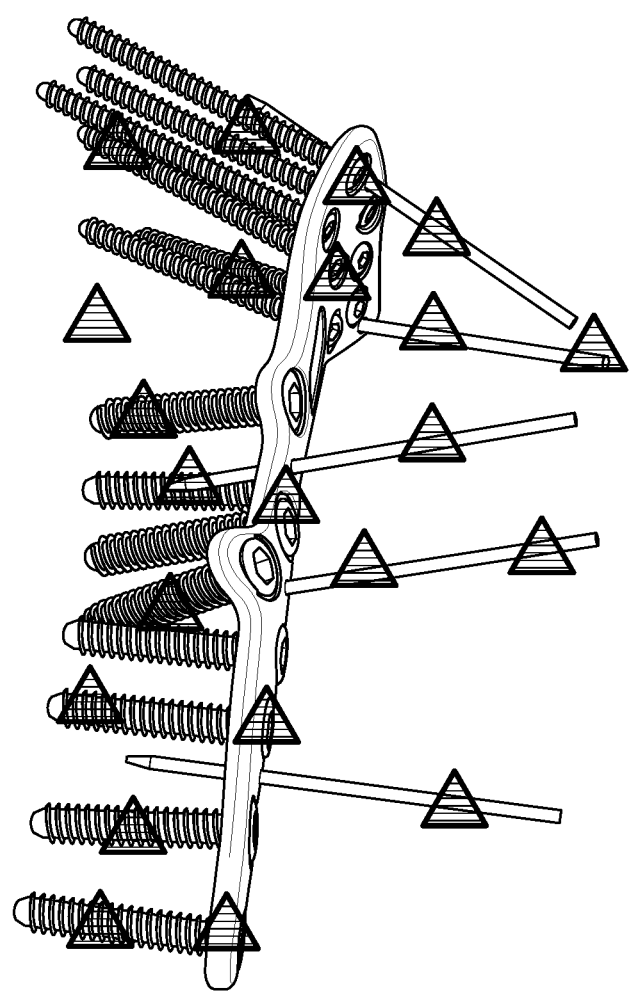

Within another embodiment plates are provided with accelerometers (and strain gauges). As illustrated in FIG. 10C, similar to pressure sensors, accelerometers (and strain gauges) can be distributed on, or within the plate at specific or randomized locations. Within certain embodiments they may be concentrated on specific locations (e.g., on both the bone and tissue surface, at the ends, and/or around screw holes). The accelerometers can be useful during placement and removal (if necessary) of the plate, for proper alignment, fit, contour, blade placement and imaging.

Accelerometers and strain gauges can also be useful after placement of a plate. For example, they can be utilized post-operatively to monitor alignment, stability, healing, patient activities, stresses across the fracture, rotation, bending, breakage, plate movement/slippage, and joint immobilization (or lack thereof).

Within another embodiment of the invention plates are provided with one or more position sensors/location marker sensors. As shown in FIG. 10A, sensors can be distributed on, or within the plate at specific or randomized locations. Within certain embodiments they may be concentrated on specific locations (e.g., on both the bone and tissue surface, plate ends, and/or around screw holes). The position sensors/location marker sensors can be useful during placement and removal (if necessary) of the plate, during movement through different tissues (for blade plates), to monitor alignment and molding to the bone surface, and in an imaging function after placement.

Position sensors/location marker sensors can also be useful after placement of a plate. For example, they can be utilized to monitor healing anatomy, and compare changes in location over time (e.g., post-surgery). They can also be utilized to monitor alignment, shifting and migration, to confirm joint immobilization, and to detect plate bending and/or breakage. Importantly, plates with position sensors/location markers can be utilized to detect movement (e.g., 'backing out') of the screw before serious complications arise.

Within yet other embodiments of the invention plates are provided with temperature sensors and or chemical sensors. Briefly, temperature and/or chemical sensors can be utilized to monitor mineralization, galvanic corrosion, tissue health, bleeding, tissue temperature, tissue integrity, and/or the presence of an infection or a developing infection [e.g., bone infections (Osteomyelitis), and/or tissue necrosis].

As should be readily evident given the disclosure provided herein, the plates of the present invention can have one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide a 'real-world' alignment of the bone, to assist in detecting mobility/immobility of the fracture (and associated joints), to monitor healing and the development of complications, to collect and compare procedure performance data over time, to evaluate patient function, and to better understand the conditions which implants are exposed to in the real world.

A2.5 Intramedullary Fixation: Rods and Nails

Intramedullary rods and nails are long metal rods which are forced into the medullary cavity of a long bone (e.g., a femur, humerus, or tibia), thereby providing greater stability and support to the bone during healing.

Intramedullary fixation of long bone fractures has been around for centuries. The earliest recorded evidence is that of an anthropologist who in the 16$^{th}$ century travelled to Mexico and witnessed Aztec physicians placing wooden sticks into the medullary canals of patients with long bone non-unions. Ivory and metal was also utilized in early treatments, although the rate of infection and complications was very high. During the 1900s, Gerhard Kuntscher believed that the same science behind the Smith-Petersen nails might work for diaphyseal fractures, and thus he developed his 'marrow nail'.

Since that time the science of intramedullary devices (e.g., rods and nails) has expanded greatly. Today there are a wide variety of intramedullary rods or nails which are designed for specific applications, including for example, interlocking nails, Küntscher nails, Ender's nail, Grosse-Kempf (GK) nails, Gamma nails, and Rush nails.

Figure 11A:
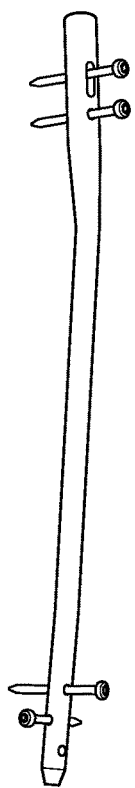
FIGS. 11A, 11B and 11C illustrate representative intramedullary rods or nails, including an intramedullary nail (FIG. 11A), placement of an intramedullary nail in the tibia (FIG. 11B), and representative sensors placed on an intramedullary nail in the tibia (FIG. 11C).
Figure 11B:
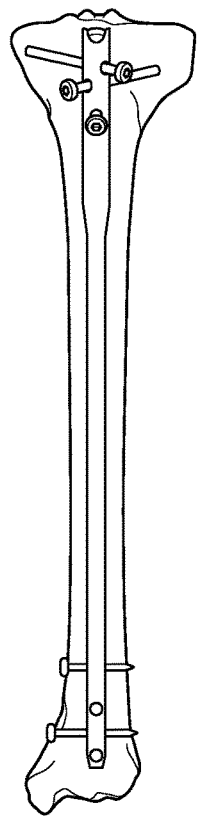
Figure 11C:
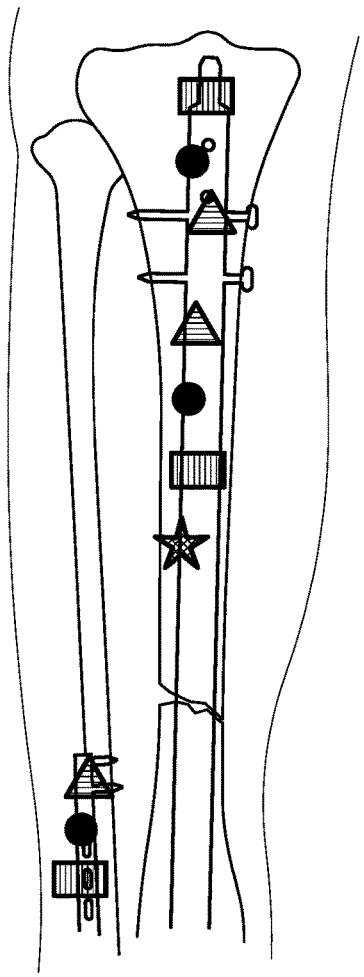
Figures 12A, 12B:
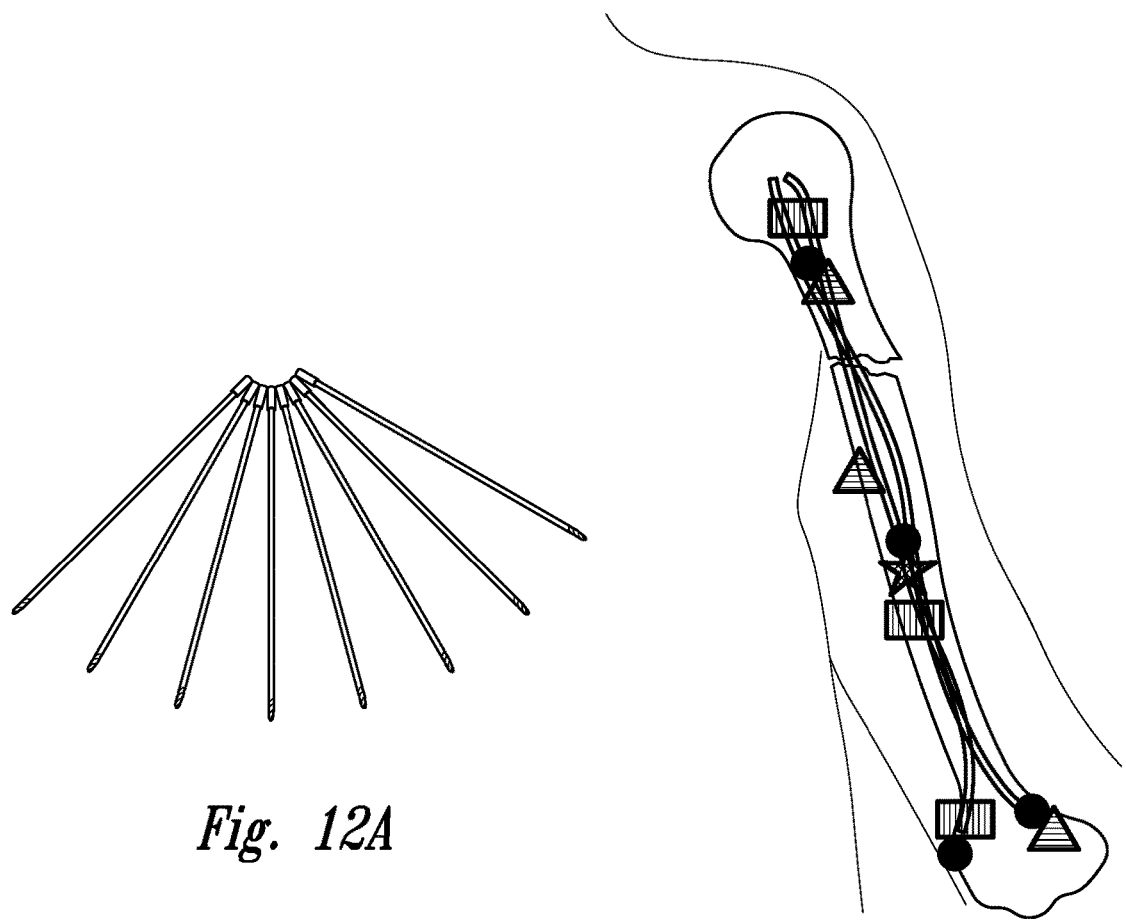
FIG. 12A illustrates a variety of representative flexible nails for intramedullary fixation.
FIG. 12B illustrates a variety of sensors placed on or within a flexible nail as placed within the humerus.

As noted above, the present invention provides intramedullary rods and nails (also referred to as "intramedullary devices" which have a variety of sensors. FIG. 11 illustrates representative intramedullary rods or nails, including an intramedullary nail (FIG. 11A), placement of an intramedullary nail in the tibia (FIG. 11B), and representative sensors placed on an intramedullary nail in the tibia (FIG. 11C). FIG. 12A illustrates a variety of representative flexible nails for intramedullary fixation. FIG. 12B illustrates a variety of sensors placed on or within a flexible nail as placed within the humerus.

Within one embodiment of the invention pressure sensors are provided on or within an intramedullary rod or nail device. The pressure sensors can be positioned within specific locations (e.g., at the ends, on or around screw holes in interlocking nails), or distributed throughout the intramedullary device. They can be utilized to assist in implanting the intramedullary nail or rod device by detecting soft tissues, bone and marrow, and or movement through tissue or bone during placement. They can also be useful after placement. For example, detection of increased pressure can indicate the potential for stress shielding or the potential for bending cracking or fracture of the rod or nail. Detection of a rapid change in pressure can indicate rod or nail breakage. Detecting a slow decrease in pressure can indicate that healing is occurring and can assist in decisions on weight bearing and rehabilitation. Monitoring the pressure around the screw holes can assist with appropriate tightening during placement; later it can be used to detect "backing out" of the screws or other complications such as breakage.

Within another embodiment intramedullary devices are provided with accelerometers (and strain gauges). Accelerometers (and strain gauges) can be distributed on, or within the intramedullary device at specific or randomized locations. Within certain embodiments they may be concentrated on specific locations (e.g., on both ends, and/or around screw holes). The accelerometers can be useful during placement and removal (if necessary) of the intramedullary device, during movement through different tissues, and for proper placement, fit, alignment, movement and imaging.

Accelerometers and strain gauges can also be useful after placement of an intramedullary device. For example, they can be utilized post-operatively to monitor alignment, stability, healing, patient activities, stresses across the fracture, axial loading, and rod/nail rotation, bending, breakage or slippage.

Within another embodiment of the invention intramedullary devices are provided with one or more position sensors/location marker sensors. The sensors can be distributed on, or within the intramedullary device at specific or randomized locations. Within certain embodiments they may be concentrated on specific locations (e.g., at the ends, and/or around screw holes). The position sensors/location marker sensors can be useful during placement and removal (if necessary) of the intramedullary device, during movement through different tissues (soft tissue, cortical bone cancellous bone, marrow, through the fracture plane), to monitor alignment, and in an imaging function after placement.

Position sensors/location marker sensors can also be useful after placement of an intramedullary device. For example, they can be utilized to monitor healing anatomy, and compare changes in location over time (e.g., post-surgery). They can also be utilized to monitor alignment, shifting and migration, to confirm fracture immobilization, and to detect rod/nail bending and/or breakage. Importantly, intramedullary devices with position sensors/location markers can be utilized to detect movement, slippage and alignment changes before serious complications arise.

Within yet other embodiments of the invention intramedullary devices are provided with temperature sensors and or chemical sensors. Briefly, temperature and/or chemical sensors can be utilized to monitor mineralization, tissue health, bleeding, tissue temperature, tissue integrity, and/or the presence of an infection or a developing infection [e.g., bone infections (Osteomyelitis), and/or tissue necrosis].

As should be readily evident given the disclosure provided herein, the intramedullary devices of the present invention can have one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide a 'real-world' alignment of the bone, to assist in detecting mobility/immobility of the fracture (and associated joints), to monitor healing and the development of complications, to collect and compare procedure performance data over time, to evaluate patient function, and to better understand the conditions which implants are exposed to in the real world.

A2.6 General Considerations

In summary, a wide variety of sensors may be placed on and/or within internal orthopedic hardware in order to provide "real time" information and feedback to the surgeon during and after the procedure, to detect proper device placement, to achieve proper fracture reduction and alignment during and after surgery, and to detect and monitor the forces the implant will be subjected to in the activities of daily life.

A3. Bone Cement and other Implantable Materials

As described herein bone cement and/or a variety of hemostats and glues can be utilized in a large number of trauma procedures. Most typically, methylmethacrylates are utilized (e.g., polymethylmethacrylate, or amethylmethacrylate-styrene copolymer), although other materials can also be utilized.

However, a wide variety of implantable materials can also be utilized (see generally US 2007/0100449). For example, suitable materials include both biocompatible polymers, therapeutic agents, and naturally occurring materials. Biocompatible polymers may be both bioabsorbable and/or nonbioabsorbable. Typically, the polymers will be synthetics (e.g., aliphatic polyesters, poly(amino acids), copoly(etheresters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly(ether urethane), copolymers of lactide (e.g., D,L lactide), glycolides, caprolactones and blends and copolymers thereof. However, in certain embodiments natural polymers can also be utilized (e.g., fibrin-based materials, collagen-based materials, hyaluronic acid-based materials, glycoprotein-based materials, cellulose-based materials, silks and combinations thereof).

Within certain embodiments of the invention the bone cement or implantable material may contain a desired agent, compound, or matrix, such as, for example, bone morphogenic protein or "BMP", bone graft material, and calcium phosphate.

The bone cement and other implantable materials described herein may contain one or more sensors, including for example, fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain embodiments the bone cement or implantable material will sensors at a density of greater than 1, 2, 3, 4, 5, 6, 7, 8, 9, 10 or 20 sensors per square centimeter; and or sensors a density of greater than 1, 2, 3, 4, 5, 6, 7, 8, 9, 10 or 20 sensors per cubic centimeter A4. Manufacturing Methods Within various embodiments of the invention, methods are also provided for manufacturing an orthopedic device or implant having one of the sensors provided herein. For example, within one embodiment of the invention sensors described herein can be placed directly onto, within or upon the orthopedic device or implant at the time of manufacture, and subsequently sterilized in a manner suitable for use in subjects.

Within further embodiments, the present disclosure provides a method of making an orthopedic device or implant by 3D printing, additive manufacturing, or a similar process whereby the orthopedic device or implant is formed from powder or filament that is converted to a fluid form that subsequently solidifies as the desired shape. For convenience, such processes will be referred to herein as printing processes or 3D printing processes. The present disclosure provide a method of making an orthopedic device or implant by a printing process, where that orthopedic device or implant includes a sensor, circuit or other feature as disclosed herein (collectively sensor or sensors). The sensor may be separately produced and then incorporated into the orthopedic device or implant during the printing process. For example, a sensor may be placed into a desired position and the printing process is carried out around the sensor so that the sensor becomes embedded in the printed spinal implant or device. Alternatively, the printing process may be started and then at appropriate times, the process is paused to allow a sensor to be placed adjacent to the partially completed spinal implant or device. The printing process is then re-started and construction of the orthopedic device or implant is completed. The software that directs the printing process may be programmed to pause at appropriate predetermined times to allow a sensor to be added to the partially printed spinal implant or device.

In addition, or alternatively, the sensor itself, or a portion thereof may be printed by the 3D printing process. Likewise, electronic connectively to, or from, or between, sensors may be printed by the 3D printing process. For example, conductive silver inks may be deposited during the printing process to thereby allow conductivity to, or from, or between sensors of a spinal implant or device, medical delivery device for a spinal implant or device. See, e.g., PCT publication nos. WO 2014/085170; WO 2013/096664; WO 2011/126706; and WO 2010/0040034 and US publication nos. US 2011/0059234; and US 2010/0037731. Thus, in various embodiments, the present disclosure provides spinal implants or devices wherein the sensor is printed onto a substrate, or a substrate is printed and a sensor is embedded or otherwise incorporated into or onto the substrate, or both the substrate and the sensor are printed by a 3D printing technique.

3D printing may be performed using various printing materials, typically delivered to the 3D printer in the form of a filament. Two common printing materials are polylactic acid (PLA) and acrylonitrile-butadiene-styrene (ABS), each being an example of a thermoplastic polymer. When strength and/or temperature resistance is particularly desirable, then polycarbonate (PC) may be used as the printing material. Other polymers may also be used. See, e.g., PCT publication nos. WO 2014/081594 for a disclosure of polyamide printing material. When metal parts are desired, a filament may be prepared from metal or metal alloy, along with a carrier material which ultimately will be washed or burned or otherwise removed from the part after the metal or metal alloy has been delivered.

When the orthopedic device or implant is of a particularly intricate shape, it may be printed with two materials. The first material is cured (using, e.g., actinic radiation) as it is deposited, while the second material is uncured and can be washed away after the spinal implant or device has been finally printed. In this way, significant hollow spaces may be incorporated into the spinal implant or device.

Additive manufacturing is a term sometimes used to encompass printing techniques wherein metal or metal allow is the material from which the desired part is made. Such additive manufacturing processes utilizes lasers and build an object by adding ultrathin layers of materials one by one. For example, a computer-controlled laser may be used to direct pinpoint beams of energy onto a bed of cobalt-chromium alloy powder, thereby melting the alloy in the desired area and creating a 10-30-micron thick layer. Adjacent layers are sequentially and repetitively produced to create the desired sized item. As needed, a sensor may be embedded into the alloy powder bed, and the laser melts the powder around the sensor so as to incorporate the sensor into the final product. Other alloys, including titanium, aluminum, and nickel-chromium alloys, may also be used in the additive manufacturing process. See, e.g., PCT publication nos. WO 2014/083277; WO 2014/074947; WO 2014/071968; and WO 2014/071135; as well as US publication nos. US 2014/077421; and US 2014/053956.

Accordingly, in one embodiment the present disclosure provides a method of fabricating sensor-containing orthopedic devices or implants, the method comprising forming at least one of a sensor and a support for the sensor using a 3D printing technique. Optionally, the 3D printing technique may be an additive manufacturing technique. In a related embodiment, the present disclosure provides an orthopedic device or implant that is produced by a process comprising a 3D printing process, such as an additive manufacturing process, where the spinal implant or device includes a sensor.

Within yet further embodiments of the invention, the spinal implants or devices provided herein can be sterilized suitable for use in a subject.

Disclosure of 3D printing processes and/or additive manufacturing is found in, for example PCT publication nos. WO 2014/020085; WO 2014/018100; WO 2013/179017; WO 2013/163585; WO 2013/155500; WO 2013/152805; WO 2013/152751; WO 2013/140147 and US publication nos. 2014/048970; 2014/034626; US 2013/337256; 2013/329258; US 2013/270750.

B. Use of Orthopedic Hardware to Deliver Therapeutic Agent(s)

As noted above, the present invention also provides drug-eluting orthopedic hardware and drug-coated orthopedic hardware which comprise one or more sensors, and which can be utilized to release a therapeutic agent (e.g., a drug) to a desired location within the body (e.g., a body tissue such as bone marrow, or sites of possible or typical infection or inflammation). Within related embodiments, a drug-eluting delivery device may be included within the orthopedic implant in order to release a desired drug upon demand (e.g., upon remote activation/demand, or based upon a timed schedule), or upon detection of an activating event (e.g., detection of an accelerometer of a significant impact event, or detection of loosening by a contact sensor) (see generally U.S. Patent App. No. 2011/0092948 entitled "Remotely Activated Piezoelectric Pump For Delivery of Biological Agents to the Intervertebral Disc and Bone", which is incorporated by reference in its entirety).

For example, within certain embodiments of the invention, biological agents can be administered along with or released from an orthopedic implant in order to increase bone growth, fibrosis or scarring within the implant. Representative examples of suitable agents include, for example, irritants, silk, wool, talcum powder, metallic beryllium, and silica. Other agents which may be released by the orthopedic implant include components of extracellular matrix, fibronectin, polylysine, ethylenevinylacetate, and inflammatory cytokines such as TGFβ, PDGF, VEGF, bFGF, TNFα, NGF, GM-CSF, IGF-a, IL-1, IL-8, IL-6, BMP and growth hormone, and adhesives such as cyanoacrylate (see U.S. Patent App. Nos. 2005/0149173 and 2005/0021126, both of which are incorporated by reference in their entirety).

Within other embodiments of the invention anti-scarring biological agents (e.g., drugs such as paclitaxel, sirolimus, or an analog or derivative of these), can be administered along with or released from an orthopedic implant in order to prevent scarring of the implant inappropriately (see, e.g., U.S. Pat. No. 7,491,188, U.S. Patent Application Nos. 2005/0152945, 2005/0187639, 2006/0079836, US 2009/0254063, US 2010/0023108, and US 2010/0042121).

Within other embodiments of the invention, anti-inflammatory agents, local anesthetics and pain-relief medications (e.g., drugs such as cortisone, dexamethasone, nonsteroidal anti-inflammatories, lidocaine, marcaine, morphine, codeine, narcotic pain relievers and analogs or derivatives of these) can be utilized to reduce post-operative pain and swelling and reduce the need for systemic pain relief therapy.

Within other embodiments a wide variety of additional therapeutic agents may be delivered (e.g., to prevent or treat an infection such as osteomyelitis or to treat another disease state such as a primary or secondary bone tumor), including for example: Anthracyclines (e.g., gentamycin, tobramycin, doxorubicin and mitoxantrone); Fluoropyrimidines (e.g., 5-FU); Folic acid antagonists (e.g., methotrexate); Podophylotoxins (e.g., etoposide); Camptothecins; Hydroxyureas, and Platinum complexes (e.g., cisplatin) (see e.g., U.S. Pat. No. 8,372,420 which is incorporated by reference in its entirety. Other therapeutic agents include beta-lactam antibiotics (e.g., the penicillins, cephalosporins, carbacephems and carbapenems); aminoglycosides (e.g., sulfonamides, quinolones and the oxazolidinones); glycopeptides (e.g., vancomycin); lincosamides (e.g., clindamycin); lipopeptides; macrolides (e.g., azithromycin); monobactams; nitrofurans; polypeptides (e.g, bacitracin); and tetracyclines.

Within preferred embodiments one or more sensors (e.g., pressure sensors, contact sensors, and/or position sensors) can be utilized to determine appropriate placement of the desired drug, as well as the quantity and release kinetics of drug to be released at a desired site.

C. Methods for Monitoring Infection

Within other embodiments orthopedic devices or implants are provided comprising one or more temperature sensors. Such orthopedic devices/implants can be utilized to measure the temperature of the orthopedic device or implant, and in the local tissue adjacent to the orthopedic device or implant. Methods are also provided for monitoring changes in temperature over time, in order to determine and/or provide notice (e.g., to a patient or a healthcare provider) that an infection may be imminent. For example, temperature sensors may be included within one or more components of the orthopedic device or implant in order to allow early detection of infection could allow preemptive treatment with antibiotics or surgical drainage and eliminate the need to surgically remove the orthopedic device or implant.

In certain embodiments of the present invention, metabolic and physical sensors can also be placed on or within the various components of a device or implant in order to monitor for rare, but potentially life-threatening complications of orthopedic device or implants. In some patients, the orthopedic device or implant and surrounding tissues can become infected; typically from bacteria colonizing the patient's own skin that contaminate the surgical field or the device surface (often *Staphylococcus aureus* or *Staphylococcus epidermidis*). Sensors such as temperature sensors (detecting temperature increases), pH sensors (detecting pH decreases), and other metabolic sensors (e.g. oxygen content, $CO_2$ content, bacterial DNA detection assays) can be used to suggest the presence of infection on or around the orthopedic device or implant.

Hence, within one embodiment of the invention methods are provided for determining an infection associated with an orthopedic implant, comprising the steps of a) providing to a patient an orthopedic implant as described herein, wherein the orthopedic implant comprises at least one temperature sensor and/or metabolic sensor, and b) detecting a change in said temperature sensor and/or metabolic sensor, and thus determining the presence of an infection. Within various embodiments of the invention the step of detecting may be a series of detections over time, and a change in the sensor is utilized to assess the presence or development of an infection. Within further embodiments a change of 0.5%, 1.0%, or 1.5% elevation of temperature or a metabolic factor over time (e.g., 0.5, 1.0, 1.5, 2.0, 2.5, 3.0, 3.5, 4 hours, 12 hours, 1 day, or 2 days) can be indicative of the presence of an infection (or a developing infection).

Within various embodiments of the invention an antibiotic may be delivered in order to prevent, inhibit or treat an infection subsequent to its detection. Representative examples of suitable antibiotics are well known, and are described above under Section B (the "Therapeutic Agents")

D. Further Uses of Sensor-Containing Orthopedic Device or Implants in Healthcare Sensors on orthopedic device or implants, and any associated medical device have a variety of benefits in the healthcare setting, and in non-healthcare settings (e.g., at home or work). For example, postoperative progress can be monitored (readings compared from day-to-day, week-to-week, etc.) and the information compiled and relayed to both the patient and the attending physician allowing rehabilitation to be followed sequentially and compared to expected (typical population) norms. Within certain embodiments, a wearable device interrogates the sensors on a selected or randomized basis, and captures and/or stores the collected sensor data. This data may then be downloaded to another system or device (as described in further detail below).

Integrating the data collected by the sensors described herein (e.g., contact sensors, position sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), range of motion and orthopedic device or implant performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation, time of day, compliance and timing of medication use (pain medications, anti-inflammatories), recent activity, patient strength, mental status, language barriers, the nature of their doctor-patient relationship, or even the patient's ability to accurately articulate their symptoms—to name just a few. Continuous monitoring and data collection can allow the patient and the physician to monitor progress objectively by supplying objective information about patient function under numerous conditions and circumstances, to evaluate how performance has been affected by various interventions (pain control, anti-inflammatory medication, rest, etc.), and to compare patient progress versus previous function and future expected function. Better therapeutic decisions and better patient compliance can be expected when both the doctor and the patient have the benefit of observing the impact of various treatment modalities on patient rehabilitation, activity, function and overall performance.

E. Generation of Power

Within certain aspects of the invention, a small electrical generation unit can be positioned along an outer, or alternatively an inner, surface of the orthopedic device or implant, or associated medical device. Briefly, a variety of techniques have been described for scavenging power from small mechanical movements or mechanical vibration. See, for example, the article entitled "Piezoelectric Power Scavenging of Mechanical Vibration Energy," by U. K. Singh et al., as published in the Australian Mining Technology Conference, Oct. 2-4, 2007, pp. 111-118, and the article entitled "Next Generation Micro-power Systems by Chandrakasan et al., as published in the 2008 Symposium on VLSI Circuits Digest of Technical Papers, pp. 1-5. See also U.S. Pat. No. 8,283,793 entitled "Device for Energy Harvesting within a Vessel," and U.S. Pat. No. 8,311,632 entitled "Devices, Methods and Systems for Harvesting Energy in the Body," all of the above of which are incorporated by reference in their entirety. These references provide examples of different types of power scavengers which can produce electricity from very small motion and store the electricity for later use. The above references also describes embodiments in which pressure is applied and released from the particular structure in order to produce electricity without the need for motion, but rather as a result of the application of high pressure. In addition, these references describe embodiments wherein electricity can be produced from pulsatile forces within the body and movements within the body.

After the electricity is generated by one or more generators, the electricity can be transmitted to any one of the variety of sensors which is described herein. For example, it can be transmitted to any of the sensors shown in Figures. It may also be transmitted to the other sensors described herein. The transmission of the power can be carried out by any acceptable technique. For example, if the sensor is physically coupled to the orthopedic device or implant, electric wires may run from the generator to the particular sensor. Alternatively, the electricity can be transmitted wirelessly in the same way that wireless smartcards receive power from closely adjacent power sources using the appropriate send and receive antennas. Such send and receive techniques of electric power are also described in the publication and the patent applications and issued U.S. patent previously described, all of which are incorporated herein by reference.

F. Medical Imaging and Self-Diagnosis of Assemblies Comprising Orthopedic Device or Implants; Predictive Analysis and Predictive Maintenance Within other aspects of the invention methods are provided for imaging the orthopedic device or implant as provided herein, comprising the steps of (a) detecting the location of one or more sensors in the orthopedic device or implant, and/or associated medical device; and (b) visually displaying the location of said one or more sensors, such that an image of the orthopedic device or implant and/or medical device is created. Within various embodiments, the step of detecting may be done over time, and the visual display may thus show positional movement over time. Within certain preferred embodiments the image which is displayed is a three-dimensional image. Within preferred embodiments the various images (e.g., 2D or 3D) may be collected and displayed in a time-sequence (e.g., as a moving image or 'movie-like' image). Within other embodiment, the imaging techniques may be utilized post-operatively in order to examine the orthopedic device or implant, and/or to compare operation and/or movement of the device over time such as during placement (intra-operatively) or during the post-operative (rehabilitative) period.

The present invention provides orthopedic device or implants and associated medical devices which are capable of imaging through the use of sensors over a wide variety of conditions. For example, within various aspects of the invention methods are provided for imaging the orthopedic device or implant (or portion thereof) or an assembly comprising the orthopedic device or implant, medical device or kit (as described herein) with sensors, comprising the steps of detecting the changes in sensors in, on, and or within the orthopedic device or implant, medical device or kit over time, and wherein the orthopedic device or implant, medical device or kit comprises sensors at a density of greater than 1, 2, 3, 4, 5, 6, 7, 8, 9, 10 or greater than 10 sensors per square centimeter. Within other aspects the orthopedic device or implant medical device or kit comprises sensors at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. Within various embodiments the at least one or more of the sensors may be placed randomly, or at one or more specific locations within the orthopedic device or implant, medical device, or kit as described herein. As noted above, a wide variety of sensors can be utilized therein, including for example, contact sensors, strain gauge sensors, pressure sensors, fluid pressure sensors, position sensors, tissue chemistry sensors, tissue metabolic sensors, mechanical stress sensors, and temperature sensors.

For example, the orthopedic device or implant, medical device, or kit comprising sensors as described herein can be utilized to image anatomy through sensors which can detect positional movement. The sensors used can also include accelerometers and motion sensors to detect movement of the orthopedic device or implant due to a variety of physical changes. Changes in the position of the accelerometers and/or motion sensors over time can be used as a measurement of changes in the position of the orthopedic device or implant over time. Such positional changes can be used as a surrogate marker of orthopedic device or implant anatomy—i.e. they can form an "image' of the orthopedic device or implant to provide information on the size, shape, integrity, alignment and location of changes to the orthopedic device or implant, and/or orthopedic device or implant movement/migration. In particular, as noted above the image data can be collected over time, in order to visually show changes (e.g., a "movie" or 'moving images", which may be in 2D or 3D).

Figure 13:
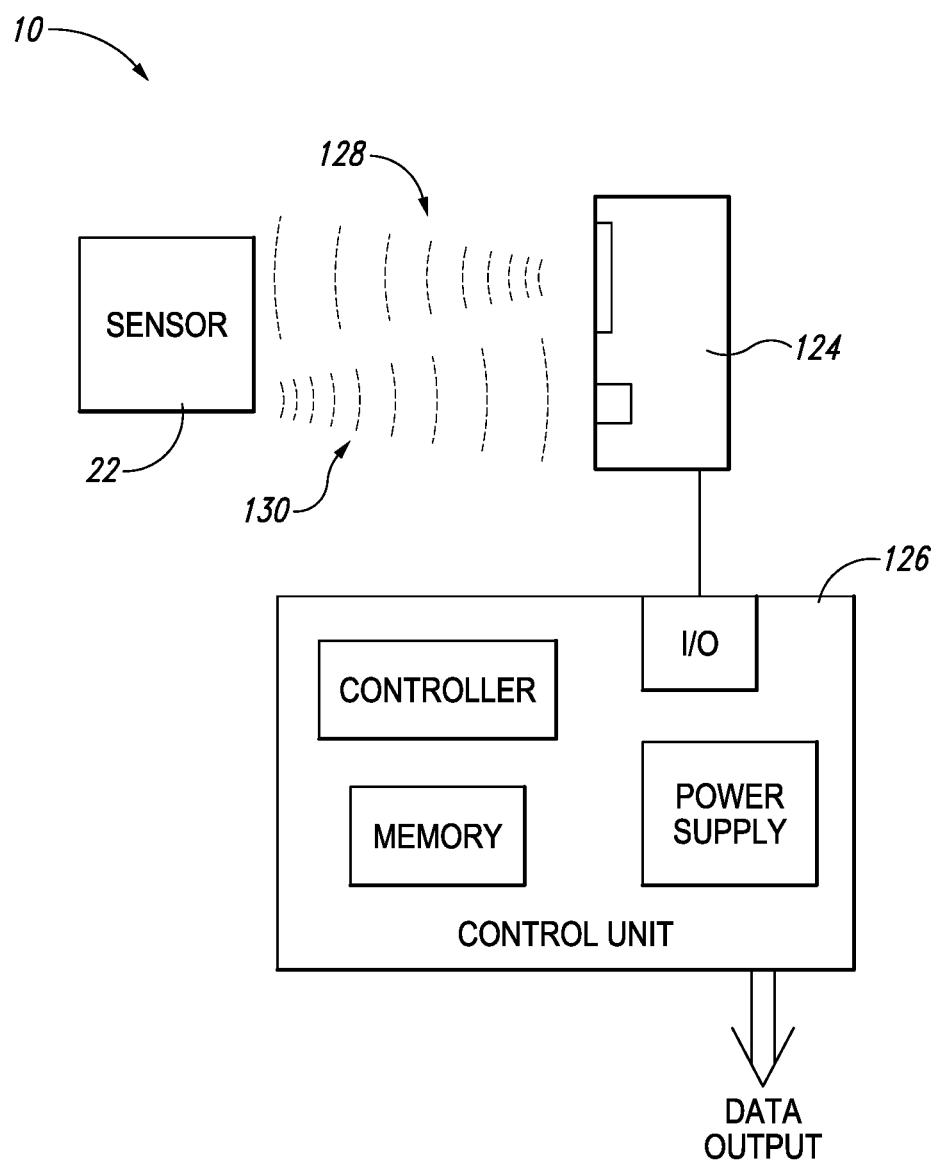
FIG. 13 illustrates an information and communication technology system embodiment arranged to process sensor data.

Certain exemplary embodiments will now be explained in more detail. One particular benefit is the live and in-situ monitoring of the patient's recovery with an orthopedic device or implant 10 having sensor 22 as shown in FIG. 13. The sensors as described herein are collecting data on a constant basis, during normal daily activities and even during the night if desired. For example, the contact sensors can obtain and report data once every 10 seconds, once a minute, or once a day. Other sensors will collect data more frequently, such as several times a second. For example, it would be expected that the temperature, contact, and/or position data could be collected and stored several times a second. Other types of data might only need to be collected by the minute or by the hour. Still other sensors may collect data only when signaled by the patient to do so (via an external signaling/triggering device) as part of "event recording"—i.e. when the patient experiences a particular event (e.g. pain, injury, instability, etc.)—and signals the device to obtain a reading at that time in order to allow the comparison of subjective/symptomatic data to objective/sensor data in an effort to better understand the underlying cause or triggers of the patient's symptoms.

In certain instances the orthopedic device or implant is of sufficient size and has more than sufficient space in order to house one or more processor circuits, CPUs, memory chips and other electrical circuits as well as antennas for sending and receiving the data. Within other embodiments, the associated medical device may be able to house the one or more processor circuits, CPUs, memory chips and other electrical circuits as well as antennas for sending and receiving the data. Processors can be programmed to collect data from the various sensors on any desired schedule as set by the medical professional. All activity can be continuously monitored post operation or post-procedure and the data collected and stored in the memory located inside the orthopedic device or implant.

A patient with an orthopedic device or implant will generally have regular medical checkups. When the patient goes to the doctor's office for a medical checkup, the doctor will bring a reading device closely adjacent to the orthopedic device or implant 10, in this example the orthopedic device or implant, in order to transfer the data from the internal circuit inside the orthopedic device or implant to the database in the physician's office. The use of wireless transmission using smartcards or other techniques is very well known in the art and need not be described in detail. Examples of such wireless transmission of data are provided in the published patent applications and patents which have been described herein. The data which has been collected (e.g., over a short period of time, over several weeks or even several months) is transferred in a few moments from the memory which is positioned in the orthopedic device or implant to the doctor's computer or wireless device. The computer therefore analyzes the data for anomalies, unexpected changes over time, positive or negative trends, and other signs which may be indicative of the health of the patient and the operability of the orthopedic device or implant. For example, if the patient has decided to go skiing or jogging, the doctor will be able to monitor the effect of such activity on the orthopedic device or implant 10, including the accelerations and strains during the event itself. The doctor can then look at the health of the orthopedic device or implant in the hours and days after the event and compare it to data prior to the event to determine if any particular event caused long term damage, or if the activities subjected the orthopedic device or implant to forces beyond the manufacturer's performance specifications for that particular orthopedic device or implant. Data can be collected and compared with respect to the ongoing and long term performance of the orthopedic device or implant from the strain gauges, the contact sensors, the surface wear sensors, or other sensors which may be present. Hence, within preferred embodiments the data can be collected over time, in order to visually show changes (e.g., a 2D or 3D "movie" or 'moving images").

In one alternative, the patient may also have such a reading device in their home which collates the data from the orthopedic device or implant on a periodic basis, such as once per day or once per week. As described above, the patient may also be able to "trigger" a device reading (via an external signaling/triggering device) as part of "event recording." Empowering the patient to follow their own rehabilitation—and enabling them to see the positive (and negative) effects of various lifestyle choices on their health and rehabilitation—can be expected to improve compliance and improve patient outcomes. Furthermore, their experience can be shared via the web with other patients to compare their progress versus expected "norms" for function and rehabilitation and alert them to signs and symptoms that should be brought to their doctor's attention. The performance of different orthopedic device or implants can be compared in different patients (different sexes, weights, activity levels, etc.) to help manufacturers design better devices and assist surgeons and other healthcare providers in the selection of the right orthopedic device or implant for specific patient types. Payers, patients, manufacturers and physicians could all benefit from the collection of this comparative information. Lastly, data accumulated at home can be collected and transmitted via the Internet to the physician's office for analysis—potentially eliminating unnecessary visits in some cases and encouraging immediate medical follow-up in others.

Figure 14:
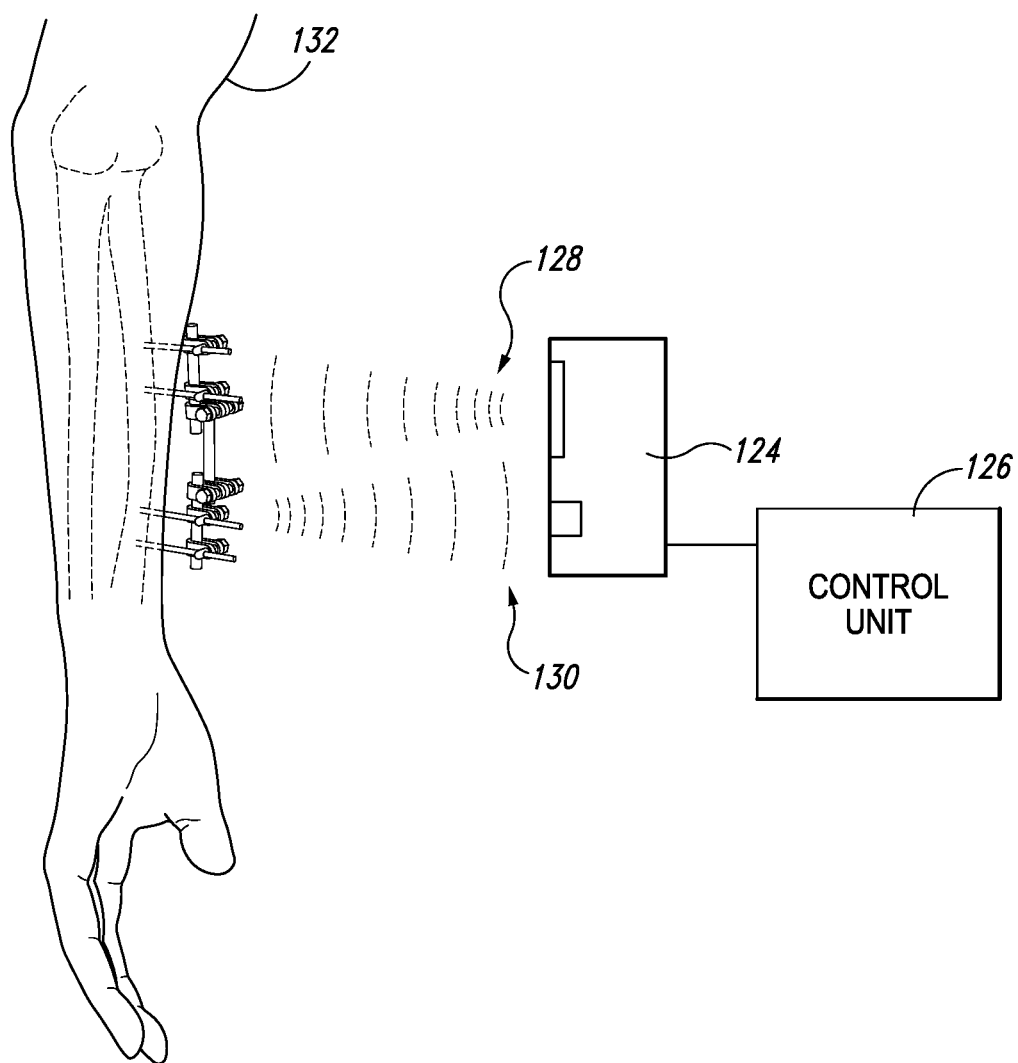
FIG. 14 is a block diagram of a sensor, interrogation module, and a control unit according to one embodiment of the invention.

G. Methods of Monitoring Assemblies Comprising Orthopedic Device or Implants As noted above, the present invention also provides methods for monitoring one or more of the orthopedic device or implants provided herein. For example, FIG. 14 illustrates a monitoring system usable with the orthopedic device or implant 10 as of the type shown in any one of the Figures described above. The monitoring system includes one or more sensors 22 an interrogation module 124, and a control unit 126. The sensor 22 can be passive, wireless type which can operate on power received from a wireless source. Such sensors of this type are well known in the art and widely available. A pressure sensor of this type might be a MEMS pressure sensor, for example, Part No. LPS331AP, sold on the open market by STMicroelectronics. MEMS pressure sensors are well known to operate on very low power and suitable to remain unpowered and idle for long periods of time. They can be provided power wirelessly on an RF signal and, based on the power received wirelessly on the RF signal, perform the pressure sensing and then output the sensed data.

In one embodiment, an electrical generation system (as described above) is provided that can be utilized to power the sensors described herein. During operation, as shown in FIG. 14, an interrogation module 124 outputs a signal 128. The signal 128 is a wireless signal, usually in the RF band, that contains power for the sensors 22 as well as an interrogation request that the sensors perform a sensing. Upon being interrogated with the signal 128, the sensors 22 powers up and stores power in onboard capacitors sufficient to maintain operation during the sensing and data reporting. Such power receiving circuits and storing on onboard capacitors are well known in the art and therefore need not be shown in detail. The appropriate sensing is carried out by the sensors 22 and then the data is output from the sensor back to the interrogation module 124 on a signal 130, where it is received at an input port of the integration module.

According to one embodiment, sufficient signal strength is provided in the initial signal 128 to provide power for the sensor and to carry out the sensing operation and output the signal back to the interrogation module 124. In other embodiments, two or more signals 128 are sent, each signal providing additional power to the sensor to permit it to complete the sensing operation and then provide sufficient power to transfer the data via the signal path 130 back to the interrogation module 124. For example, the signal 128 can be sent continuously, with a sensing request component at the first part of the signal and then continued providing, either as a steady signal or pulses to provide power to operate the sensor. When the sensor is ready to output the data, it sends a signal alerting the interrogation module 124 that data is coming and the signal 128 can be turned off to avoid interference. Alternatively, the integration signal 128 can be at a first frequency and the output signal 130 at a second frequency separated sufficiently that they do not interfere with each other. In a preferred embodiment, they are both the same frequency so that the same antenna on the sensor can receive the signal 128 and send signal 130.

The interrogation signal 128 may contain data to select specific sensors on the orthopedic device or implant. For example, the signal 128 may power up all sensors on the orthopedic device or implant at the same time and then send requests for data from each at different selected times so that with one interrogation signal 128 provided for a set time, such as 1-2 seconds, results in each of the sensors on the orthopedic device or implant collecting data during this time period and then, at the end of the period, reporting the data out on respective signals 130 at different times over the next 0.5 to 2 seconds so that with one interrogation signal 128, the data from all sensors 22 is collected.

The interrogation module 124 is operating under control of the control unit 126 which has a microprocessor for the controller, a memory, an I/O circuit to interface with the interrogation module and a power supply. The control unit may output data to a computer or other device for display and use by the physician to treat the subject.

FIG. 14 illustrates the operation according to a one embodiment within a subject. The subject has an outer skin 132. As illustrated in FIG. 14, the interrogation module 124 and control unit 126 are positioned outside the skin 132 of the subject. The interrogation signal 128 passes through the skin of the subject with a wireless RF signal, and the data is received on a wireless RF signal 130 from the sensors within the orthopedic device or implant 10 back to the interrogation module 124. While the wireless signal can be in any frequency range, an RF range is preferred. A frequency in the VLF to LF ranges of between 3-1300 kHz is preferred to permit the signal to be carried to sufficient depth inside the body with low power, but frequencies below 3 kHz and above 1300 kHz can also be used. The sensing does not require a transfer of large amounts of data and low power is preferred; therefore, a low frequency RF signal is acceptable. This also avoids competition from and inadvertent activation by other wireless signal generators, such as bluetooth, cell phones and the like.

Figure 15:
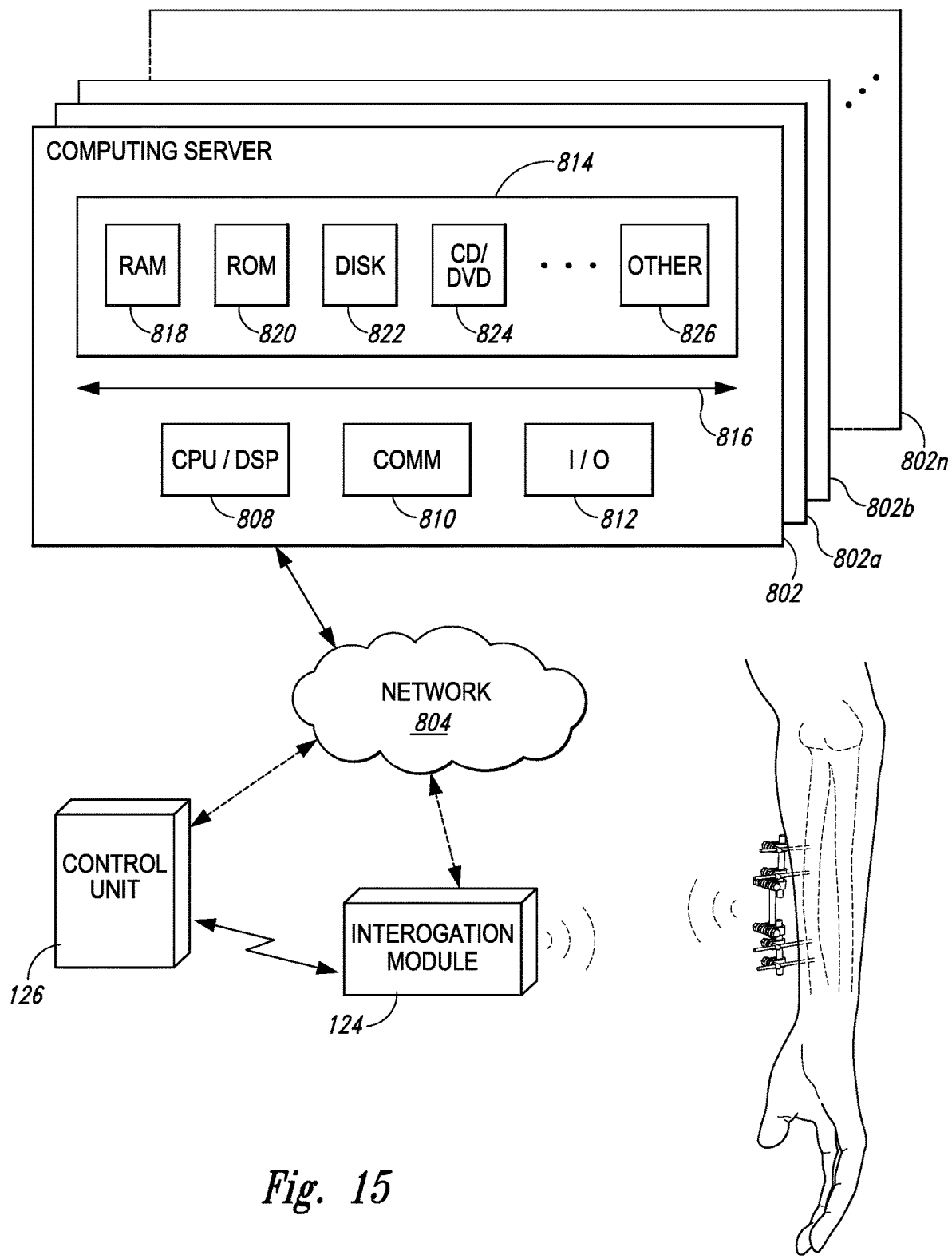
FIG. 15 is a schematic illustration of one or more sensors positioned on the orthopedic implant within a subject which is being probed for data and outputting data, according to one embodiment of the invention.

H. Collection, Transmission, Analysis, and Distribution of Data from Assemblies Comprising Orthopedic Device or Implants FIG. 15 illustrates one embodiment of an information and communication technology (ICT) system 800 arranged to process sensor data (e.g., data from the sensors 22). In FIG. 15, the ICT system 800 is illustrated to include computing devices that communicate via a network 804, however in other embodiments, the computing devices can communicate directly with each other or through other intervening devices, and in some cases, the computing devices do not communicate at all. The computing devices of FIG. 15 include computing servers 802, control units 126, interrogation units 124, and other devices that are not shown for simplicity.

In FIG. 15, one or more sensors 22 communicate with an interrogation module 124. The interrogation module 124 of FIG. 15 is directed by a control unit 126, but in other cases, interrogation modules 124 operates autonomously and passes information to and from sensors 22. One or both of the interrogation module 124 and control unit 126 can communicate with the computing server 802.

Within certain embodiments, the interrogation module and/or the control unit may be a wearable device on the subject. The wearable device (e.g., a watch-like device, a wrist-band, or other device that may be carried or worn by the subject) can interrogate the sensors over a set (or random) period of time, collect the data, and forward the data on to one or more networks (804). Furthermore, the wearable device may collect data of its own accord which can also be transmitted to the network. Representative examples of data that may be collected include location (e.g., a GPS), body or skin temperature, and other physiologic data (e.g., pulse). Within yet other embodiments, the wearable device may notify the subject directly of any of a number of prescribed conditions, including but not limited to possible or actual failure of the device.

The information that is communicated between an interrogation module 124 and the sensors 22, may be useful for many purposes as described herein. In some cases, for example, sensor data information is collected and analyzed expressly for the health of an individual subject. In other cases, sensor data is collected and transmitted to another computing device to be aggregated with other data (for example, the sensor data from 22 may be collected and aggregated with other data collected from a wearable device (e.g., a device that may, in certain embodiments, include GPS data and the like).

FIG. 15 illustrates aspects of a computing server 802 as a cooperative bank of servers further including computing servers 802a, 802b, and one or more other servers 802n. It is understood that computing server 802 may include any number of computing servers that operate individually or collectively to the benefit of users of the computing servers.

In some embodiments, the computing servers 802 are arranged as cloud computing devices created in one or more geographic locations, such as the United States and Canada. The cloud computing devices may be created as MICROSOFT AZURE cloud computing devices or as some other virtually accessible remote computing service.

An interrogation module 124 and a control unit 126 are optionally illustrated as communicating with a computing server 802. Via the interrogation module 124 or control unit 126, sensor data is transferred to (and in addition or alternatively from) a computing server 802 through network 804.

The network 804 includes some or all of cellular communication networks, conventional cable networks, satellite networks, fiber-optic networks, and the like configured as one or more local area networks, wide area networks, personal area networks, and any other type of computing network. In a preferred embodiment, the network 804 includes any communication hardware and software that cooperatively works to permit users of computing devices to view and interact with other computing devices.

Computing server 802 includes a central processing unit (CPU) digital signal processing unit (DSP) 808, communication modules 810, Input/Output (I/O) modules 812, and storage module 814. The components of computing server 802 are cooperatively coupled by one or more buses 816 that facilitate transmission and control of information in and through computing server 802. Communication modules 810 are configurable to pass information between the computer server 802 and other computing devices (e.g., computing servers 802*a*, 802*b*, 802*n*, control unit 126, interrogation unit 124, and the like). I/O modules 812 are configurable to accept input from devices such as keyboards, computer mice, trackballs, and the like. I/O modules 812 are configurable to provide output to devices such as displays, recorders, LEDs, audio devices, and the like.

Storage module 814 may include one or more types of storage media. For example, storage module 814 of FIG. 15 includes random access memory (RAM) 818, read only memory (ROM) 810, disk based memory 822, optical based memory 8124, and other types of memory storage media 8126. In some embodiments one or more memory devices of the storage module 814 has configured thereon one or more database structures. The database structures may be used to store data collected from sensors 22.

In some embodiments, the storage module 814 may further include one or more portions of memory organized a non-transitory computer-readable media (CRM). The CRM is configured to store computing instructions executable by a CPU 808. The computing instructions may be stored as one or more files, and each file may include one or more computer programs. A computer program can be standalone program or part of a larger computer program. Alternatively or in addition, each file may include data or other computational support material for an application that directs the collection, analysis, processing, and/or distribution of data from sensors (e.g., orthopedic device or implant sensors). The sensor data application typically executes a set of instructions stored on computer-readable media.

It will be appreciated that the computing servers shown in the figures and described herein are merely illustrative and are not intended to limit the scope of the present invention. Computing server 802 may be connected to other devices that are not illustrated, including through one or more networks such as the Internet or via the Web that are incorporated into network 804. More generally, a computing system or device (e.g., a "client" or "server") or any part thereof may comprise any combination of hardware that can interact and perform the described types of functionality, optionally when programmed or otherwise configured with software, including without limitation desktop or other computers, database servers, network storage devices and other network devices, PDAs, cell phones, glasses, wrist bands, wireless phones, pagers, electronic organizers, Internet appliances, television-based systems (e.g., using set-top boxes and/or personal/digital video recorders), and various other products that include appropriate inter-communication capabilities. In addition, the functionality provided by the illustrated system modules may in some embodiments be combined in fewer modules or distributed in additional modules. Similarly, in some embodiments the functionality of some of the illustrated modules may not be provided and/or other additional functionality may be available.

In addition, while various items are illustrated as being stored in memory or on storage while being used, these items or portions of them can be transferred between memory and other storage devices for purposes of memory management and/or data integrity. In at least some embodiments, the illustrated modules and/or systems are software modules/systems that include software instructions which, when executed by the CPU/DSP 808 or other processor, will program the processor to automatically perform the described operations for a module/system. Alternatively, in other embodiments, some or all of the software modules and/or systems may execute in memory on another device and communicate with the illustrated computing system/device via inter-computer communication.

Furthermore, in some embodiments, some or all of the modules and/or systems may be implemented or provided in other manners, such as at least partially in firmware and/or hardware means, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), and the like. Some or all of the systems, modules, or data structures may also be stored (e.g., as software instructions or structured data) on a transitory or non-transitory computer-readable storage medium 814, such as a hard disk 822 or flash drive or other non-volatile storage device 8126, volatile 818 or non-volatile memory 810, a network storage device, or a portable media article (e.g., a DVD disk, a CD disk, an optical disk, a flash memory device, etc.) to be read by an appropriate input or output system or via an appropriate connection. The systems, modules, and data structures may also in some embodiments be transmitted as generated data signals (e.g., as part of a carrier wave or other analog or digital propagated signal) on a variety of computer readable transmission mediums, including wireless-based and wired/cable-based mediums. The data signals can take a variety of forms such as part of a single or multiplexed analog signal, as multiple discrete digital packets or frames, as a discrete or streaming set of digital bits, or in some other form. Such computer program products may also take other forms in other embodiments. Accordingly, the present invention may be practiced with other computer system configurations.

In FIG. 15, sensor data from, e.g., sensors 22 is provided to computing server 802. Generally speaking, the sensor data, represents data retrieved from a known subject and from a known sensor. The sensor data may possess include or be further associated with additional information such as the USI, UDI, a time stamp, a location (e.g., GPS) stamp, a date stamp, and other information. The differences between various sensors is that some may include more or fewer data bits that associate the data with a particular source, collection device, transmission characteristic, or the like.

In some embodiments, the sensor data may comprise sensitive information such as private health information associated with a specific subject. Sensitive information, for example sensor data from sensors e.g., 22, may include any information that an associated party desires to keep from wide or easy dissemination. Sensitive information can stand alone or be combined with other non-sensitive information. For example, a subject's medical information is typically sensitive information. In some cases, the storage and transmission of a subject's medical information is protected by a government directive (e.g., law, regulation, etc.) such as the U.S. Health Insurance Portability and Accountability Act (HIPPA).

As discussed herein, a reference to "sensitive" information includes information that is entirely sensitive and information that is some combination of sensitive and non-sensitive information. The sensitive information may be represented in a data file or in some other format. As used herein, a data file that includes a subject's medical information may be referred to as "sensitive information." Other information, such as employment information, financial information, identity information, and many other types of information may also be considered sensitive information.

A computing system can represent sensitive information with an encoding algorithm (e.g., ASCII), a well-recognized file format (e.g., PDF), or by some other format. In a computing system, sensitive information can be protected from wide or easy dissemination with an encryption algorithm.

Generally speaking, sensitive information can be stored by a computing system as a discrete set of data bits. The set of data bits may be called "plaintext." Furthermore, a computing system can use an encryption process to transform plaintext using an encryption algorithm (i.e., a cipher) into a set of data bits having a highly unreadable state (i.e., cipher text). A computing system having knowledge of the encryption key used to create the cipher text can restore the information to a plaintext readable state. Accordingly, in some cases, sensitive data (e.g., sensor data 806a, 806b) is optionally encrypted before being communicated to a computing device.

In one embodiment, the operation of the information and communication technology (ICT) system 800 of FIG. 15 includes one or more sensor data computer programs stored on a computer-readable medium. The computer program may optionally direct and/or receive data from one or more orthopedic device or implant sensors orthopedic device or implanted in one or more subjects. A sensor data computer program may be executed in a computing server 802. Alternatively, or in addition, a sensor data computer program may be executed in a control unit 126, an interrogation unit 124.

In one embodiment, a computer program to direct the collection and use of orthopedic device or implant sensor data is stored on a non-transitory computer-readable medium in storage module 814. The computer program is configured to identify a subject who has a wireless orthopedic device or implant inserted in his or her body. The wireless orthopedic device or implant may include one or more wireless sensors.

In some cases, the computer program identifies one subject, and in other cases, two or more subjects are identified. The subjects may each have one or more wireless orthopedic device or implants, and each wireless orthopedic device or implant may have one or more wireless sensors of the type described herein.

The computer program is arranged to direct the collection of sensor data from the wireless orthopedic device or implant devices. The sensor data is generally collected with a wireless interrogation unit 124. In some cases, the program communicates with the wireless interrogation unit 124. In other cases, the program communicates with a control unit 126, which in turn directs a wireless interrogation unit 124. In still other cases, some other mechanism is used direct the collection of the sensor data.

Once the sensor data is collected, the data may be further processed. For example, in some cases, the sensor data includes sensitive subject data, which can be removed or disassociated with the data. The sensor data can be individually stored (e.g., by unique sensor identification number, device number, etc.) or aggregated together with other sensor data by sensor type, time stamp, location stamp, date stamp, subject type, other subject characteristics, or by some other means.

The following pseudo-code description is used to generally illustrate one exemplary algorithm executed by a computing server 802 and generally described herein with respect to FIG. 15:

```
Start
    Open a secure socket layer (SSL)
    Identify a subject
    Communicate with a predetermined control unit
    Request sensor data from the subject via the control unit
    Receive sensor data
    If the sensor data is encrypted
        THEN decrypt the sensor data
    Store encrypted data in the selected storage locations
    Aggregate the sensor data with other sensor data
    Store encrypted data in the selected storage locations
    Maintain a record of the storage transaction
    Perform post storage actions
End
```

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, ambulance, truck, locomotive, tank, armored personnel carrier, etc.), (c) a building (e.g., a home, hospital, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., AT&T, T-Mobile, Verizon.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

In conclusion, orthopedic device or implants utilizing a variety of sensors can be utilized to serve a variety of critical clinical functions, such as safe, accurate and less traumatic placement and deployment of the orthopedic device or implant, procedural and post-operative "real time" imaging of the orthopedic device or implant and the surrounding anatomy, the early identification of the development of orthopedic device or implant complications (often prior to becoming evident by other medical diagnostic procedures), and the patient's overall health status and response to treatment. Currently, post-operative (both in hospital and out-patient) evaluation of orthopedic device or implant patients is through patient history, physical examination and medical monitoring that is supplemented with diagnostic imaging studies as required. However, most of the patient's recuperative period occurs between hospital and office visits and the majority of data on daily function goes uncaptured; furthermore, monitoring patient progress through the use of some diagnostic imaging technology can be expensive, invasive and carry its own health risks (the use of nuclear isotopes or certain dyes, radiation exposure). It can, therefore, be very difficult to accurately measure and follow the development or worsening of symptoms and evaluate "real life" orthopedic device or implant performance, particularly as they relate to patient activity levels, exercise tolerance, and the effectiveness of rehabilitation efforts and medications.

At present, neither the physician nor the patient has access to the type of "real time," continuous, objective, orthopedic device or implant performance measurements that they might otherwise like to have. Being able to monitor in situ orthopedic device or implant function, integrity, anatomy and physiology can provide the physician with valuable objective information during office visits; furthermore, the patient can take additional readings at home at various times (e.g. when experiencing pain, during exercise, after taking medications, etc.) to provide important complementary clinical information to the doctor (which can be sent to the healthcare provider electronically even from remote locations). From the perspective of the patient, being able to monitor many of these same parameters at home allows them to take a more proactive role in their care and recovery and provide him or her with either an early warning indicator to seek medical assistance or with reassurance.

In one alternative, the patient may have a reading device in their home which collates the data from the orthopedic device or implant on a periodic basis, such as once per day or once per week. For example, within certain embodiments the devices and systems provided herein can instruct or otherwise notify the patient, or a permitted third-party as to deviations (e.g., greater than 10%, 20%, 25%, 50%, 70%, and or 100%) from normal, and/or, set parameters. In addition to empowering the patient to follow their own rehabilitation—and enabling them to see the positive (and negative) effects of various lifestyle choices on their health and rehabilitation—such information access can be expected to improve compliance and improve patient outcomes. Furthermore, their recovery experience can be shared via the web with other patients to compare their progress versus expected "norms" for function and rehabilitation and alert them to signs and symptoms that should be brought to their doctor's attention. From a public health perspective, the performance of different orthopedic device or implants can be compared in different patients (different sexes, disease severity, activity levels, concurrent diseases such as hypertension and diabetes, smoking status, obesity, etc.) to help manufacturers design better orthopedic device or implants and assist physicians in the selection of the right orthopedic device or implant for a specific patient types. Payers, patients, manufacturers and physicians could all benefit from the collection of this comparative information. Poor and dangerous products could be identified and removed from the market and objective long-term effectiveness data collected and analyzed. Lastly, data accumulated at home can be collected and transmitted via the Internet to the physician's office for analysis—potentially eliminating unnecessary visits in some cases and encouraging immediate medical follow-up in others.

CONVENTIONS

In general, and unless otherwise specified, all technical and scientific terms used herein shall have the same meaning as those commonly understood by one of ordinary skill in the art to which the embodiment pertains. For convenience, the meanings of selected terms are provided below, where these meanings are provided in order to aid in describing embodiments identified herein. Unless stated otherwise, or unless implicit from the context in which the term is used, the meanings provided below are the meanings intended for the referenced term.

Embodiment examples or feature examples specifically provided are intended to be exemplary only, that is, those examples are non-limiting on an embodiment. The term "e.g." (latin, exempli gratia) is used herein to refer to a non-limiting example, and effectively means "for example".

Singular terms shall include pluralities and plural terms shall include the singular, unless otherwise specified or required by context. For example, the singular terms "a", "an" and "the" include plural referents unless the context clearly indicates otherwise. Similarly, the term "or" is intended to include "and" unless the context clearly indicates otherwise.

Except in specific examples provided herein, or where otherwise indicated, all numbers expressing quantities of a component should be understood as modified in all instances by the term "about", where "about" means ±5% of the stated value, e.g., 100 refers to any value within the range of 95-105.

The terms comprise, comprising and comprises are used to identify essential features of an embodiment, where the embodiment may be, for example, a composition, device, method or kit. The embodiment may optionally contain one or more additional unspecified features, and so the term comprises may be understood to mean includes.

The following are some specific numbered embodiments of the systems and processes disclosed herein. These embodiments are exemplary only. It will be understood that the invention is not limited to the embodiments set forth herein for illustration, but embraces all such forms thereof as come within the scope of the above disclosure.

1) A medical device, comprising a cast, and a sensor.
2) A medical device, comprising a brace, and a sensor.
3) A medical device, comprising a support or sling, and a sensor.
4) A medical device, comprising a tensor, and a sensor.
5) An implantable medical device, comprising an orthopedic pin, and a sensor.
6) An implantable medical device, comprising a K-wire, and a sensor.
7) An implantable medical device, comprising an orthopedic screw, and a sensor.
8) An implantable medical device, comprising an orthopedic plate and a sensor.
9) An implantable medical device, comprising an intramedullary device and a sensor.
10) An implantable medical device, comprising a polymer and a sensor.
11) The medical device according to embodiment 10 wherein said polymer is selected from the group consisting of a polymethylmethacrylate, a methylmethacrylate-styrene copolymer, fibrin, polyethylene glycol, carboxymethylcellulose, and polyvinylalcohol.

12) The medical device according to any one of embodiments 1 to 11 wherein said sensor is located within said implant.
13) The medical device according to any one of embodiments 1 to 11 wherein said sensor is located on said implant.
14) The medical device according to any one of embodiments 1 to 13 wherein said device is sterile.
15) The medical device according to any one of embodiments 1 to 14 wherein said sensor is a contact sensor.
16) The medical device according to any one of embodiments 1 to 14 wherein said sensor is a pressure sensor.
17) The medical device according to any one of embodiments 1 to 14 wherein said sensor is an accelerometer sensor.
18) The medical device according to embodiment 17 wherein said accelerometer detects acceleration, tilt, vibration, shock and or rotation.
19) The medical device according to any one of embodiments 1 to 14 wherein said sensor is a temperature sensor.
20) The medical device according to any one of embodiments 1 to 14 wherein said sensor is a mechanical stress sensor.
21) The medical device according to any one of embodiments 1 to 14 wherein said sensor is selected from the group consisting of position sensors, chemical microsensors, and tissue metabolic sensors.
22) The medical device according to any one of embodiments 1 to 22 further comprising:
an electronic processor positioned upon and/or inside the orthopedic device or implant or medical device that is electrically coupled to sensors.
23) The medical device according to embodiment 22 wherein the electric coupling is a wireless coupling.
24) The medical device according to embodiment 22 further including:
a memory coupled to the electronic processor and positioned upon and/or inside the orthopedic device or implant or medical device.
25) The medical device according to any one of embodiments 1 to 24 wherein said sensor is a plurality of sensors which are positioned on or within said medical device at a density of greater than 1, 2, 3, 4, 5, 6, 7, 8, 9, 10 or 20 sensors per square centimeter.
26) The medical device according to any one of embodiments 1 to 24 wherein said sensor is a plurality of sensors which are positioned on or within said medical device at a density of greater than 1, 2, 3, 4, 5, 6, 7, 8, 9, 10 or 20 sensors per cubic centimeter.
27) A method comprising:
obtaining data from sensors positioned at a plurality of locations between on and/or within the medical device according to any one of embodiments 1 to 26 of a patient;
storing the data in a memory device located on or within the medical device; and
28) The method according to embodiment 27 further comprising the step of analyzing said data.
29) A method for detecting and/or recording an event in a subject with the medical device according to any one of embodiments 1 to 26, comprising the step of interrogating at a desired point in time the activity of one or more sensors within the medical device, and recording said activity.
30) The method according to embodiment 29 wherein the step of interrogating is performed by a subject which has said medical device.
31) The method according to embodiment 29 or 30 wherein said recording is performed on a wearable device.
32) The method according to any one of embodiments 29, 30 or 31, wherein said recording, or a portion thereof, is provided to a health care provider.
33) A method for imaging the medical device in the bone, comprising the steps of
(a) detecting the location of one or more sensors in the medical device according to any one of embodiments 1 to 26; and
(b) visually displaying the location of said one or more sensors, such that an image of the medical device, or a portion thereof, in the bone is created.
34) The method according to embodiment 33 wherein the step of detecting occurs over time.
35) The method according to embodiment 33 or 34, wherein said visual display shows changes in the positions of said sensors over time, and/or changes in temperature of the sensors or surrounding tissue over time.
36) The method according to any one of embodiments 33 to 35 wherein said visual display is a three-dimensional image of said medical device in the bone.
37) A method for inserting the orthopedic device or implant according to any one of embodiments 1 to 26, comprising the steps of
(a) inserting an implantable medical device according to any one of embodiments 1 to 26 into a subject; and
(b) imaging the placement of said medical device according to the method of any one of embodiments 33 to 36.
38) A method for examining the orthopedic device or implant according to any one of embodiments 1 to 26 which has been previously inserted into a patient, comprising the step of imaging the orthopedic device or implant according to the method of any one of embodiments 33 to 36.
39) A method of monitoring an orthopedic device or implant within a subject, comprising:
(a) transmitting a wireless electrical signal from a location outside the body to a location inside the subject's body;
(b) receiving the signal at a sensor positioned on an orthopedic device or implant according to any one of embodiments 1 to 26 located inside the body;
(c) powering the sensor using the received signal;
(d) sensing data at the sensor; and
(e) outputting the sensed data from the sensor to a receiving unit located outside of the body.
40) The method according to embodiment 39 wherein said receiving unit is a watch, wrist band, cell phone or glasses.
41) The method according to embodiments 39 or 40 wherein said receiving unit is located within a subject's residence or office.
42) The method according to embodiments any one of embodiments 39 to 41 wherein said sensed data is provided to a health care provider.
43) The method according to any one of embodiments 39 to 42 wherein said sensed data is posted to one or more websites.
44) A non-transitory computer-readable storage medium whose stored contents configure a computing system to perform a method, the method comprising:

(a) identifying a subject, the identified subject having at least one wireless orthopedic device or implant according to any one of embodiments 1 to 26, each wireless orthopedic device or implant having one or more wireless sensors;
(b) directing a wireless interrogation unit to collect sensor data from at least one of the respective one or more wireless sensors; and
(c) receiving the collected sensor data.

45) The non-transitory computer-readable storage medium of embodiment 44 whose stored contents configure a computing system to perform a method, the method further comprising:
(a) identifying a plurality of subjects, each identified subject having at least one wireless orthopedic device or implant, each wireless orthopedic device or implant having one or more wireless sensors;
(b) directing a wireless interrogation unit associated with each identified subject to collect sensor data from at least one of the respective one or more wireless sensors;
(c) receiving the collected sensor data; and
(d) aggregating the collected sensor data.

46) The non-transitory computer-readable storage medium of embodiment 44 whose stored contents configure a computing system to perform a method, the method further comprising:
(a) removing sensitive subject data from the collected sensor data; and
(b) parsing the aggregated data according to a type of sensor.

47) The non-transitory computer-readable storage medium of embodiment 44 whose stored contents configure a computing system to perform a method, wherein directing the wireless interrogation unit includes directing a control unit associated with the wireless interrogation unit.

48) The non-transitory computer readable storage medium according to any one of embodiments 44 to 47, wherein said orthopedic device or implant is according to any one of embodiments 1 to 26.

49) The storage medium according to any one of embodiments 44 to 48 wherein said collected sensor data is received on a watch, wrist band, cell phone or glasses.

50) The storage medium according to any one of embodiments 44 to 49 wherein said collected sensor data is received within a subject's residence or office.

51) The storage medium according to any one of embodiments 44 to 50 wherein said collected sensed data is provided to a health care provider.

52) The storage medium according to any one of embodiments 44 to 51 wherein said sensed data is posted to one or more websites.

53) The method according to any one of embodiments 39 to 43, or storage medium according to any one of embodiments 44 to 52, wherein said data is analyzed.

54) The method or storage medium according to embodiment 53 wherein said data is plotted to enable visualization of change over time.

55) The method or storage medium according to embodiments 53 or 54 wherein said data is plotted to provide a three-dimensional image.

55) A method for determining degradation of an orthopedic device or implant, comprising the steps of a) providing to a subject an orthopedic device or implant according to any one of embodiments 1 to 26, and b) detecting a change in a sensor, and thus determining degradation of the orthopedic device or implant.

56) The method according to embodiment 55 wherein said sensor is capable of detecting one or more physiological and/or locational parameters.

57) The method according to embodiments 55 or 56 wherein said sensor detects a location within the subject.

58) The method according to any one of embodiments 55 to 58 wherein said sensor moves from its original location, thereby indicating degradation of the orthopedic device or implant.

59) The method according to any one of embodiments 55 to 59 wherein the step of detecting is a series of detections over time.

60) A method for determining an infection associated with an orthopedic device or implant, comprising the steps of a) providing to a subject an orthopedic device or implant according to any one of embodiments 1 to 26, wherein said orthopedic device or implant comprises at least one temperature sensor and/or metabolic sensor, and b) detecting a change in said temperature sensor and/or metabolic sensor, and thus determining the presence of an infection.

61) The method according to embodiment 60 wherein the step of detecting is a series of detections over time.

62) The method according to embodiments 60 or 61 wherein said change is greater than a 1% change over the period of one hour.

63) The method according to any one of embodiments 60 to 62 wherein said change is a continually increasing temperature and/or metabolic activity over the course of 4 hours.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of manufacturing a spinal implant where the spinal implant comprises a sensor, the method comprising:
performing an additive manufacturing process to create a partially created printed spinal implant;
embedding the sensor into a powder bed on the partially created printed spinal implant and melting the powder around the sensor;
performing an additive manufacturing process on the partially created printed spinal implant to create an electrical connection with the sensor;
performing an additive manufacturing process on the partially created printed spinal implant to create a printed spinal implant having a hollow space;
housing an electrical component in the hollow space; and
electrically coupling the electrical connection and the electrical component.

2. The method of claim 1 wherein,
a. the additive manufacturing process is commenced and thereafter, at appropriate times;
b. the additive manufacturing process is paused to allow the sensor to be embedded into the powder bed; and thereafter
c. the additive manufacturing process is re-started and construction of the printed spinal implant is completed.

3. The method of claim 1 wherein the sensor is not prepared by the additive manufacturing process.

4. The method of claim 1 wherein the sensor or a portion thereof is prepared by the additive manufacturing process.

5. The method of claim 1 wherein the electrical connection with the sensor is provided by conductive silver ink deposited during the additive manufacturing process.

6. The method of claim 1 wherein a thermoplastic is used during the additive manufacturing process to create the printed spinal implant.

7. The method of claim 6 wherein the thermoplastic comprises acrylonitrile-butadiene-styrene (ABS).

8. The method of claim 1 wherein a metal or metal alloy is used during the additive manufacturing process to create the printed spinal implant.

9. The method of claim 8 wherein the metal or metal alloy is selected from the group consisting of cobalt-chromium alloy, titanium, aluminum, and nickel-chromium alloys.

10. The method of claim 1 further comprising sterilizing the printed spinal implant.

11. The method of claim 1 wherein the sensor is positioned within the printed spinal implant.

12. The method of claim 1 wherein the sensor is positioned on the printed spinal implant.

13. The method of claim 1 wherein the sensor is an accelerometer.

14. The method of claim 1 wherein the electrical component is an electronic processor.

15. The method of claim 1 wherein the sensor is a plurality of sensors which are positioned on or within the printed spinal implant at a density of one of 1, 2, 3, 4, 5, 6, 7, 8, 9, 10 or 20 sensors per cubic centimeter.

16. A printed spinal implant comprising a sensor, the printed spinal implant prepared by an additive manufacturing process according to the method of claim 1.

* * * * *